(12) United States Patent
Yamakawa et al.

(10) Patent No.: US 7,924,969 B2
(45) Date of Patent: Apr. 12, 2011

(54) X RAY CT SYSTEM

(75) Inventors: Keisuke Yamakawa, Kokubunji (JP); Hironori Ueki, Hachioji (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 12/668,244

(22) PCT Filed: Dec. 21, 2007

(86) PCT No.: PCT/JP2007/074695
§ 371 (c)(1),
(2), (4) Date: Jan. 8, 2010

(87) PCT Pub. No.: WO2009/008102
PCT Pub. Date: Jan. 15, 2009

(65) Prior Publication Data
US 2010/0226474 A1 Sep. 9, 2010

(30) Foreign Application Priority Data
Jul. 11, 2007 (JP) .................................. 2007-181725

(51) Int. Cl.
*A61B 6/00* (2006.01)
(52) U.S. Cl. ........................ 378/5; 378/98.11; 378/98.12
(58) Field of Classification Search ............. 378/5, 98.9, 378/98.11, 98.12
See application file for complete search history.

(56) References Cited

U.S. PATENT DOCUMENTS

| | | | |
|---|---|---|---|
| 3,965,358 A * | 6/1976 | Macovski ......................... | 378/5 |
| 5,187,658 A * | 2/1993 | Cline et al. ...................... | 382/128 |
| 2009/0028287 A1* | 1/2009 | Krauss et al. ..................... | 378/4 |

FOREIGN PATENT DOCUMENTS

| | | |
|---|---|---|
| JP | 2004-065975 | 3/2004 |
| JP | 2004-147863 | 5/2004 |
| JP | 2004-174253 | 6/2004 |
| JP | 2006-520223 | 9/2006 |
| JP | 2007-044275 | 2/2007 |
| JP | 2007-044520 | 2/2007 |
| JP | 2007-508040 | 4/2007 |
| JP | 2007-111526 | 5/2007 |

OTHER PUBLICATIONS

Raz Carmi et al.; Material Separation with Dual-Layer CT; IEEE Nuclear Science Symposium Conference Record M03-367; 2005; pp. 1876-1878.

* cited by examiner

*Primary Examiner* — Edward J Glick
*Assistant Examiner* — Alexander H Taningco
(74) *Attorney, Agent, or Firm* — Antonelli, Terry, Stout & Kraus, LLP.

(57) ABSTRACT

The dual energy X-ray CT apparatus automatically optimizes a map for separation to achieve a high degree of separation accuracy and a reduction of dose.

An X-ray attenuation coefficient acquired in the dual energy X-ray CT system is applied to a map for separation which represents a relationship between the X-ray attenuation coefficient and a composition of an object, thereby separating the composition of the object. The map formation unit for separation calculates an existing probability of each composition for each combination of multiple types of X-ray attenuation coefficients, and determines the composition having the largest existing probability as the composition corresponding to the combination of the X-ray attenuation coefficients, thereby forming the map for separation. This configuration allows a formation of the map for separation with respect to each imaging condition, and high degree of accuracy in separating composition can be achieved.

14 Claims, 16 Drawing Sheets

X RAY CT SYSTEM

TECHNICAL FIELD

The present invention relates to an X-ray CT system, and more particularly, it relates to a technique for achieving a high degree of accuracy in separating a composition of an object, and a technique for reducing a dose.

BACKGROUND ART

An X-ray CT system is a device for measuring a computed tomographic image (hereinafter, referred to as "CT image"), and density of the image represents an X-ray attenuation coefficient (hereinafter, referred to as "attenuation coefficient"). According to a technological innovation of recent years, it is becoming possible to acquire a large quantity of CT images. As a result, in order to efficiently utilize the large quantity of CT images, it is of growing importance to have a function for automatically separating a composition of the object by the use of a computer. However, it is sometimes difficult to achieve such automatic separation of compositions (materials) which include X-ray attenuation coefficients being close to each other, as in the case of bone, organs, and vessels of a clinical material, for instance.

As a technique to solve this problem, there is suggested a dual energy imaging (hereinafter, referred to as "DE method"). A dual energy X-ray CT system which performs imaging according to the DE method irradiates the object with at least two types of X-rays having different energy spectra, and acquires CT images respectively based on the X-rays of two types or more. The two or more CT images being obtained show different values of the X-ray attenuation coefficient in the corresponding area of objects, respectively. This is because the X-ray attenuation coefficient of each composition depends on the energy spectrum of the X-ray being irradiated. Therefore, by using a map for separation obtained in advance, where the X-ray attenuation coefficient in an area of an object is associated with the composition, as to the X-rays of two types or more, it is possible to obtain an image which separates a composition (material) of the object area. As thus described, the use of the X-rays having two or more types of energy spectra allows the separation of the composition, though it has been difficult to separate the material by using the X-ray attenuation coefficient of the X-ray having only one type of energy spectrum. Such map for separation can be formed in advance by experiment or simulation.

The DE method is incorporated in an X-ray CT system used for a bomb test, which is installed for example at an airport, customs, or the like, and it is employed for separating a composition with reference to an atomic number and density information. In addition, the patent document 1 and the patent document 2 disclose that in a clinical-use X-ray CT system employed in a medical facility, separation is made between calcification in vessels and a bone, and between blood and soft plaque, or the like, by using image data of X-rays having two types of energy spectra. In the technique as disclosed in the non-patent document 1, a map for separation is formed by experiment or simulation, thereby separating calcium from a contrast medium.

[Patent Document 1]
Japanese Unexamined Patent Application Publication No. 2004-174253
[Patent Document 2]
Japanese Unexamined Patent Application Publication No. 2004-065975
[Non-Patent Document 1]
Raz Carmi, et al., "Material Separation with Dual-Layer CT", in Proc. Conf. Rec. IEEE Nuclear Science Symp., M03-367, 2005

DISCLOSURE OF THE INVENTION

Problem to be Solved by the Invention

In a conventional dual energy X-ray CT system, a standard for separation such as a map for separation, and an X-ray condition (a combination of X-ray energy and X-ray output amount) have not been optimized necessarily in association with an measured region (referred to as "separated target region"). Therefore, there have been problems such as deterioration in separation accuracy and increase of dose.

The map for separation may include descriptions being different for each combination of shooting conditions such as the separated target region and the X-ray condition. Therefore, in order to achieve a highly accurate separation, it is necessary to employ an optimum map for separation in association with each combination of the imaging condition. However, there are enormous numbers of combinations as to the imaging condition such as the separated target region and the X-ray condition. Consequently, it is necessary to prepare the huge numbers of maps for separation if the conventional method is employed where the map for separation is formed in advance by experiment and calculation, and thus it is not easy to put this method into practice. Therefore, under the present circumstances, several representative maps for separation are prepared in advance, and these maps are used as substitutes even for the case of another imaging condition. Consequently, an appropriate map for separation cannot be selected, and accordingly, the separation accuracy is deteriorated.

As for the X-ray condition, it is desirable that this condition can be automatically optimized according to a designation by a user. However, in effect, an operator configures the settings empirically. Therefore, it is not possible to perform irradiation under the optimum X-ray condition, and this may result in the increase of dose.

An object of the present invention is to optimize the map for separation in the dual energy X-ray CT system so as to achieve a highly accurate separation. In addition, by using the present technique, the separation accuracy equivalent to that of the conventional technique can be ensured with less dosage, thereby enabling a reduction of dose.

Means to Solve the Problems

In order to achieve the object above, according to the present invention, an X-ray CT system as described below is provided.

In other words, the X-ray CT system according to a first aspect of the present invention includes, an X-ray irradiation unit for irradiating X-rays having multiple types of different energy spectra, an X-ray detection unit for detecting the X-rays after passing through an object, an image calculation unit for calculating an image of X-ray attenuation coefficients respectively for the multiple types of X-rays based on each detection signal from the X-ray detection unit, a separation calculator for applying to a separation map which indicates a relationship between multiple types of X-ray attenuation coefficients and a composition of the object, values of the X-ray attenuation coefficients in association with a corresponding area in the image of multiple types of X-ray attenuation coefficients, so that the composition of the area is separated, a map formation unit for separation to form the separation map, and an input unit for accepting from an operator an input regarding an X-ray irradiation condition of the X-ray irradiation unit and multiple compositions to be separated, wherein, the map formation unit for separation performs arithmetic processing to obtain existing probabilities of the multiple compositions under the X-ray irradiation condition being inputted in the input unit, and forms the map for separation based on the existing probabilities. As thus described, the X-ray CT system according to the first aspect of the present invention is able to form the map for separation in response to the X-ray condition being inputted in the input unit, and therefore, separation of the composition can be performed with a high degree of accuracy by the use of an optimum map for separation.

For example, the map formation unit for separation as described above may have a configuration to calculate the existing probabilities of multiple compositions with respect to each combination of the multiple types of X-ray attenuation coefficients, and determine a composition having the largest existing probability as a composition corresponding to the combination of the X-ray attenuation coefficients, thereby forming the map for separation.

In a second aspect of the present invention, for example, the map formation unit for separation obtains functions, each indicating a variation of the existing probability of each of the compositions, under the X-ray irradiation condition being inputted in the input unit, assuming the multiple types of X-ray attenuation coefficients as variables, depicts as a boundary, a position where the functions each indicating the variation of the existing probability of each of the compositions are crossing, in the space of the map for separation, with coordinate axes respectively of the multiple types of X-ray attenuation coefficients, and accordingly, forms the map for separation in which multiple areas separated by the boundary correspond to the multiple compositions, respectively. Consequently, it is possible to form the map for separation in response to the X-ray irradiation condition being inputted in the input unit, thereby achieving a highly accurate separation of the composition by the use of the optimum map for separation.

In a third aspect of the present invention, for example, the map formation unit for separation obtains functions, each indicating a variation of the existing probability of each of the compositions, under the X-ray irradiation condition being inputted in the input unit, assuming the multiple types of X-ray attenuation coefficients as variables, depicts a boundary at a predetermined position based on the functions indicating the variation of the existing probability, in the space of the map for separation with coordinate axes respectively of the multiple types of X-ray attenuation coefficients, and accordingly, forms the map for separation in which multiple areas separated by the boundary correspond to the multiple compositions, respectively. Consequently, it is possible to form the map for separation in response to the X-ray irradiation condition being inputted in the input unit, thereby achieving a highly accurate separation of the composition by the use of the optimum map for separation.

In the third aspect, the map formation unit for separation has a configuration to obtain error rates as to all the compositions according to a predetermined formula, by using the function indicating the variation of the existing probability and the position of the boundary, and determines the position where the error rate is minimized as the position of the boundary.

In the aforementioned first, second, and third aspects of the invention, the map formation unit for separation, for instance, includes a data storage unit which stores in advance, an average of X-ray attenuation coefficient and a standard deviation of the X-ray attenuation coefficient, with respect to each X-ray irradiation condition, as to the multiple compositions acceptable by the input unit, reads out from the data storage unit, the average of X-ray attenuation coefficient and the standard deviation of the X-ray attenuation coefficient associated with the X-ray irradiation condition accepted from an operator by the input unit, and substitutes the read information into a predetermined formula, thereby obtaining the existing probability by calculation.

On this occasion, the input unit accepts a setting of an X-ray tube voltage and a quantity of X-ray tube current with respect to each of the multiple types of X-rays, for instance, as the X-ray irradiation condition. In this invention, the quantity of X-ray tube current is a value in units obtained by multiplying an electric current (mA) by time (sec), for example, so that the unit of mA·sec is obtained. The data storage unit stores the average of X-ray attenuation coefficient for each X-ray tube voltage acceptable by the input unit and the standard deviation of the X-ray attenuation coefficient per quantity of X-ray tube current. The map formation unit for separation uses the standard deviation of the X-ray attenuation coefficient per quantity of X-ray tube current, the quantity of X-ray tube current set in the input unit, and a predetermined formula, thereby obtaining the standard deviation of the X-ray attenuation coefficient by calculation.

In the aforementioned second aspect of the invention, the map formation unit for separation obtains a ratio of erroneous determination occurrence as to the compositions respectively associated with two areas separated by the boundary, by calculation using the function indicating the variation of the existing probabilities of the two compositions, the position of the boundary, and a predetermined formula, and when the ratio of erroneous determination occurrence is larger than a predetermined threshold, it is possible to combine the areas associated with the two areas on the map for separation, so that these areas are separated as one composition. Consequently, the compositions with a low degree of separation accuracy can be regarded as the same composition, thereby enhancing the separation accuracy.

In the second and third aspects of the invention, the input unit may accept the settings, for instance, as to only a part of the X-ray condition, which is necessary for forming the map for separation. For this case, the map formation unit for separation generates multiple candidate values as to the other part of the X-ray irradiation condition. Then, the maps for separation are formed for the multiple candidate values respectively, and as to each of the multiple types of maps for separation being obtained, the ratio of erroneous determination occurrence is obtained as to the composition in all the maps for separation, by calculation using the function indicating the variation of the existing probability, the position of the boundary, and a predetermined formula, thereby allowing the map for separation having the minimum ratio of erroneous determination occurrence to be selected. Accordingly, the candidate value for the selected map for separation can be selected as an optimum value of the X-ray irradiation condition, thereby achieving optimization of the X-ray irradiation condition.

It is possible to display the optimum value of the X-ray irradiation condition being selected for the operator, showing that it is the optimum X-ray irradiation condition. Furthermore, the X-ray irradiation unit may perform irradiation of X-rays automatically using the optimum value of the X-ray condition, so as to acquire the image of X-ray attenuation coefficient.

As the aforementioned candidate value, a quantity of X-ray tube current of the X-ray irradiation unit can be taken as an example, and accordingly the quantity of X-ray tube current is allowed to be optimized.

By way of example, the input unit may accept a setting of total irradiated dose of multiple types of X-rays, as the X-ray irradiation condition. On this occasion, the map formation unit for separation candidate values of irradiated dose respectively for the multiple types of X-rays, so that the total amount of the irradiated dose of the multiple types of X-rays satisfies the total irradiated dose being set. Alternatively, for example, the input unit accepts a setting of exposed dose according to multiple types of X-rays, and the map formation unit for separation may generate candidate values of irradiated dose respectively for the multiple types of X-rays, so that the total exposure on the object who is subjected to the irradiation of the multiple types of X-rays corresponds to the exposed dose. Consequently, the operator is allowed to set the X-ray condition easily, by using the total irradiated dose and the exposed dose.

BEST MODE FOR CARRYING OUT THE INVENTION

Hereinafter, one embodiment of the present invention will be explained in detail with reference to the accompanying drawings. It is to be noted that in the entire drawings, elements having corresponding functions are labeled the same, and tedious explanation will not be made.

First Embodiment

A dual energy X-ray CT system according to the first embodiment will be explained. As shown by the schematic configuration of FIG. 1, the X-ray CT system incorporates an input means 101, an imaging means 102, and an image generation means 103. The input means 101 includes an input unit of imaging condition 110, a map formation unit for separation 111, and a storage unit of material parameters 112. The imaging means 102 includes an imaging control unit 113, an X-ray irradiation unit 1, an X-ray detection unit 2, a gantry 5, and an object-installation table 7. The image generation means 103 includes a data acquisition unit 114, a reconstruction unit 115, a material separation unit 116, and an image display unit 117. It is to be noted here that the input means 101 and the image generation means 103 are not necessarily merged with the X-ray CT system, and such operations may be implemented by a second device which is connected via a network.

One example of hardware configuration for implementing the dual energy X-ray CT system as shown in FIG. 1 will be explained with reference to FIG. 2. As shown in FIG. 2, the input unit of imaging condition 110 in the input means 101 includes a keyboard 120, a mouse 121, a tablet, a touch panel, and the like. The map formation unit for separation 111 incorporates a central processing unit 122, a memory 123, and the like. The central processing unit 122 expands and starts a predetermined program stored in advance in the memory 123 and performs processing for forming the map for separation. The storage unit of material parameters 112 is made up of a HDD (Hard Disk Drive) 124, and the like. It is to be noted here that each of the constitutional elements is connected via a data bus 1101.

The X-ray irradiation unit 1 of the imaging means 102 includes an X-ray tube 3. The X-ray detection unit 2 includes an X-ray detector 4. A circular-shaped aperture 9 is provided at the center of the gantry 5, for placing the object 8 and the table 7 therein. The gantry 5 incorporates a rotating plate 6 equipped with the X-ray tube 3 and the X-ray detector 4, and a drive mechanism, not illustrated, for the rotation of the rotating plate 6. The table 7 is provided with a drive mechanism, not illustrated, for adjusting a position of the object with respect to the gantry 5. The imaging control unit 113 incorporates an X-ray controller 126 for controlling the X-ray tube 3, and a gantry controller 125, and a table controller 127. The gantry controller 125 controls a rotary drive of the rotating plate 6. The table controller 127 controls a drive of the table 7.

A distance between an X-ray originating point of the X-ray tube 3 and an X-ray input plane of the X-ray detector 4 may be set to 1,000 mm as a representative example. A diameter of the aperture 9 of the gantry 5 may be set to 700 mm as a representative example. An amount of time required for the rotation of the rotating plate 6 may be set to 1.0 s/time as a representative example. A publicly known X-ray detector made up of a scintillator, a photo diode, and the like, may be employed as the X-ray detector 4. The X-ray detector 4 has a configuration where a large number of detection elements are arranged in the shape of circular arc at an equal distance from the X-ray tube 3, and the number of elements (the number of channels) is 950, for instance. The size of each detection element in the direction of channel is 1 mm, for instance. The number of imaging times by the imaging means 102 per one rotation is 900, and one-time imaging is performed every time when the rotating plate 6 rotates by 0.4 degrees. The specifications described above are not limited to those values, and they may be variously changed according to the configuration of the X-ray CT system.

The data acquisition unit 114 of the image generation means 103 includes a data acquisition system (DAS) 128. The DAS 128 converts a detection result from the X-ray detector 4 into a digital signal. The reconstruction unit 115 and the material separation unit 116 incorporate the central processing unit 122, the memory 123, and the HDD 124. The central processing unit 122 and the memory 123 expand and start a predetermined program, thereby performing various processing such as image reconstruction process and separation process. The HDD 124 and the like perform storing data and inputting/outputting data. The image display unit 117 is made up of a monitor 129 such as a liquid crystal display and a CRT. It is to be noted that each of the constitutional elements is connected via the data bus 1103.

Next, an operation of the X-ray CT system according to the first embodiment will be explained. The X-ray CT system is provided with both a function for performing an imaging according to the DE method, and a function for performing general imaging. In the imaging according to the DE method, an input mode and a real imaging mode are performed in sequence. The input mode is a mode for allowing an operator to input an imaging condition such as a separated target region and an X-ray tube voltage, and obtaining an optimum map for separation by calculation based on the imaging condition. The real imaging mode is a mode for generating a CT image by the irradiation with X-rays based on the imaging condition inputted by the input mode, and thereafter, separating a material of the CT image (a composition if the object 8 is not clinical), by using the optimum map for separation obtained by the input mode. A selection of the mode is performed by the operator via the mouse 121, the keyboard 120, or the like. In the present embodiment, the map for separation is formed in the input mode as to the imaging condition which is used in the real imaging mode. Therefore, the map for separation can be optimized, achieving a high degree of separation accuracy and reduction of dose. Hereinafter, the operations in both modes will be explained.

The input mode is performed in the following order; (1) setting the imaging condition and (2) forming the map for separation. The input mode is executed by the input unit of imaging condition 110, the map formation unit for separation 111, and the storage unit of material parameters 112, which are incorporated in the input means 101 as shown in FIG. 1.

(1) Set Imaging Condition

The input unit of imaging condition 110 displays an input screen as shown in FIG. 3 on the monitor 129 or another monitor. While viewing this screen, the operator manipulates the mouse 121, the keyboard 120, or the like, constituting the input unit of imaging condition 110, thereby setting the separated target region, types of multiple materials to be separated being contained in the separated target region, an X-ray tube voltage $E_L$ and a quantity of X-ray tube current $I_L$, upon irradiation with lower X-ray energy, and an X-ray tube voltage $E_H$ and a quantity of X-ray tube current $I_H$, upon irradiation with higher X-ray energy. In this invention, the quantity of X-ray tube current is a value in units obtained by multiplying an electric current (mA) by time (sec), for example, so that the unit of mA·sec is obtained.

The input screen as shown in FIG. 3 includes a select list of separating region 130 for selecting the separated target region, a select list of separating material 131 for selecting a material to be separated, and an X-ray condition input area 132 for setting the X-ray tube voltage and the quantity of X-ray tube current respectively associated with a lower X-ray energy output amount, and a higher X-ray energy output amount. The operator selects the separated target region in the select list of separating region 130 in the screen as shown in FIG. 3. By way of example, the region can be selected from the thorax, abdomen, head, neck, spine, hip joint, extremities, and the like. It is further possible to configure the select list of separating region 130 to select not only the region, but also a material constituting the region, such as the heart, adipose, and vessel.

In addition, the operator makes a selection from the select list of separating material 131; a material for inspection applications such as a contrast medium, various plaques, calcification, tumor, a puncture device, and a catheter, and a material such as a bone, a vessel, and various organs. On this occasion, as for the material which is able to be described in the form of numerical values such as a density of the contrast medium, such numerical values are entered in the numerical value entry field in the select list of separating material 131. In the X-ray condition input area 132, each of the following values are entered; the X-ray tube voltage $E_H$ and the quantity of X-ray tube current $I_H$ upon irradiation with higher X-ray energy, and the X-ray tube voltage $E_L$ and the quantity of X-ray tube current $I_L$ upon irradiation with lower X-ray energy.

It is to be noted that the screen for inputting the imaging condition is not limited to the screen configuration as shown in FIG. 3, and there is no restriction as far as the screen has a configuration which allows settings of the separated target region, the material, the X-ray tube voltage, and the quantity of X-ray tube current. If the imaging condition is stored in advance, it is possible to read out the data to use. On such an occasion as this, it is not necessary for the operator to enter the data every time when the imaging is performed. In the screen example as shown in FIG. 3, setting of the X-ray condition including two types of energy spectra, high and low, is configured, but it is further possible to perform imaging according to the DE method by using three or more types of X-rays. On this occasion, it is further possible to configure such that the operator is allowed to add fields of the X-ray tube voltage and the quantity of X-ray tube current for the setting.

(2) Form a Map for Separation

As the processing procedure shown in FIG. 4, the map formation unit for separation 111 obtains an optimum map for separation by calculation, based on an existing probability of the X-ray attenuation coefficient in each material (referred to as "distribution of X-ray attenuation coefficient"), according to the imaging condition such as the separated target region, the X-ray tube voltage, the quantity of X-ray tube current, and the like, which are inputted in the input unit of imaging condition 110 (steps 201 to 204). This calculation is performed by using the X-ray attenuation coefficient of each material and the standard deviation of the X-ray attenuation coefficient, with respect to each imaging condition, which are stored in the storage unit of material parameters 112, in advance.

As shown in FIG. 5, the map for separation formed here is a two-dimensional map having a value of attenuation coefficient of lower X-ray energy $\mu_L$ and a value of attenuation coefficient of higher X-ray energy $\mu_H$, respectively on the x-axis and the y-axis, and it is divided into areas 51, 52, and 53, by the boundary 50. The areas 51, 52, and 53 respectively correspond to different materials (compositions), such as a bone, organs, and a vessel filled contrast medium. Therefore, as to a pixel corresponding to an image having the attenuation coefficient of lower X-ray energy and a pixel corresponding to an image having the attenuation coefficient of higher X-ray energy, both being imaged by the real imaging mode, a value of the attenuation coefficient of lower X-ray energy $\mu_L$ and a value of the attenuation coefficient of higher X-ray energy $\mu_H$, respectively indicated by the images, are obtained. The areas 51, 52, and 53 are obtained, which contain the points specifying those values above on the map for separation, thereby separating the material corresponding to each area as the material of the pixel included in the image of the X-ray attenuation coefficient. The map for separation shows the areas 51, 52, and 53 being different in shape by the boundary thereof with respect to each combination of the imaging condition (an X-ray tube voltage E, a quantity of X-ray tube current I). Therefore, in the present embodiment, the map for separation is formed by calculation as to the imaging condition being inputted (steps 201 and 204).

As shown in FIG. 4, the map formation unit for separation 111 brings from the input unit of imaging condition 110, the separated target region, the types of materials to be separated (N units), data of the X-ray tube voltages $E_L$ and $E_H$ of the X-ray tube 3, respectively corresponding to lower X-ray energy and higher X-ray energy, and thereafter, accesses the storage unit of material parameters 112. Accordingly, values of the parameters (an average of attenuation coefficient $\mu_{ave}$ associated with the X-ray tube voltages $E_L$, $E_H$, and a standard deviation $\sigma_0$ of the X-ray attenuation coefficient per quantity of X-ray tube current) are read out, which are necessary for calculating the map for separation, and which are associated with the imaging condition being taken in (step 201). Consequently, it is possible to obtain the average of attenuation coefficients $\mu_{aveL}$ and $\mu_{aveH}$, associated with the X-ray tube voltages $E_L$ and $E_H$, respectively, and noise standard deviations $\sigma_{0L}$ and $\sigma_{0H}$ per quantity of X-ray tube current of each material.

As shown in FIG. 6, the storage unit of material parameters 112 stores a table of material 140 as a database in advance, indicating an average of attenuation coefficient $\mu_{ave}$ associated with the X-ray tube voltage which is previously obtained by an experiment or simulation for each material, and a standard deviation $\sigma_0$ of X-ray attenuation coefficient per quantity of X-ray tube current, which is associated with the X-ray tube voltage. FIG. 6 shows a table of bone 141 and a table of vessel filled contrast medium 142, as examples of the table of material 140 which is stored in the storage unit of material parameters 112. The configuration of the database is not limited to that of FIG. 6, and any other configuration is applicable, as far as it has a configuration for storing the X-ray tube voltage, the average of attenuation coefficient, and the noise standard deviation per quantity of X-ray tube current, for each material.

Next, the quantity of X-ray tube current $I_L$ and $I_H$ inputted by the operator from the input unit of imaging condition 110 are taken in, and the standard deviations $\sigma_L$ and $\sigma_H$ of the X-ray attenuation coefficient are obtained according to the formulas; $\sigma_L = \sigma_{0L}/(\sqrt{I_L})$, $\sigma_H = \sigma_{0H}/(\sqrt{I_H})$ (step 202). Then, a two-dimensional distribution of X-ray attenuation coefficient $\mu(x, y)$ is calculated using a predefined expression, on the basis of the average of attenuation coefficients $\mu_{aveL}$ and $\mu_{aveH}$ and the standard deviations $\sigma_L$ and $\sigma_H$ which are obtained in step 201 and step 202 (step 203). In here, the two-dimensional distribution of X-ray attenuation coefficient $\mu(x, y)$ is approximately obtained, assuming the average of attenuation coefficients $\mu_{aveL}$ and $\mu_{aveH}$ as a center according to the two-dimensional Gaussian distribution as expressed by the formula 1 as shown below (step 203). The two-dimensional distribution of attenuation coefficient $\mu(x, y)$ is a function indicating a variation of the existing probability of the material on the x-y plane.

$$\mu(x, y) = \frac{1}{2\pi\sigma_L\sigma_H}\exp\left\{-\frac{(x-\mu_{aveL})^2}{2\sigma_L^2} - \frac{(y-\mu_{aveH})^2}{2\sigma_H^2}\right\} \quad \text{[Formula 1]}$$

Here, it is to be noted that x and y are values on the coordinate axes x, y of the map for separation as shown in FIG. 5, and x is associated with the attenuation coefficient of lower X-ray energy $\mu_L$, and y is associated with the attenuation coefficient of higher X-ray energy $\mu_H$. It is further possible to employ any other expression for the distribution of X-ray attenuation coefficient using various functions, such as a multinomial expression, exponential function, and Lorenz function, without being limited to the expression of the two-dimensional Gaussian distribution as indicated by the formula 1.

The two-dimensional distribution of X-ray attenuation coefficient $\mu(x, y)$ is obtained with respect to each material inputted in the input unit of imaging condition 110 by the operator. When the number of materials is N, $\mu_k(x, y)$ represents the distribution of X-ray attenuation coefficient of the k-th material (here, k=1, 2 ... N).

Next, the two-dimensional space of the map for separation is divided into predetermined pixels each having a minute size. With respect to each pixel, values (frequencies) of the distribution of X-ray attenuation coefficient $\mu_k(x, y)$ (here, k=1, 2 ... N) are compared as to each of N materials on the coordinate (x, y) of the pixels. The material having the largest distribution of X-ray attenuation coefficient $\mu_k(x, y)$ is decided as the material of the pixel on the coordinate (x, y). The material is determined for all the pixels within the map for separation, thereby forming the map for separation (step 204).

The map for separation being formed is transferred from the map formation unit for separation 111 to the material separation unit 116, and it is stored in the HDD 124 and the like, being constitutional elements of the material separation unit 116.

Next, with reference to FIG. 2, an operation of the X-ray CT system in the real imaging mode will be explained. In the real imaging mode, the operator designates an imaging position via the mouse 121, the keyboard 120, and the like, thereafter gives a directive to start imaging, and then, the imaging is performed under the condition which is set in the input unit of imaging condition 110 during the input mode by the operator, including the separated target region, two types of X-ray tube voltages, high and low, and the quantity of X-ray tube current for each of the X-ray tube voltages. Specifically, according to the control by the table controller 127, the table 7 moves the object 8 in approximately vertical direction with respect to the rotating plate 6, and stops moving at the time when the imaging position of the rotating plate 6 agrees with the imaging position being designated. This completes installation of the object 8. On the other hand, the gantry controller 125 activates the drive motor simultaneously with the directive to start imaging, and starts rotation of the rotating plate 6. When the rotation of the rotating plate 6 comes into a constant-speed state and the installation of the object 8 is completed, the gantry controller 125 instructs the time when the X-ray is irradiated by the X-ray tube 3 and the time when the imaging is performed by the X-ray detector 4, and then starts the imaging.

The imaging is performed during the period when the rotating plate 6 makes two rotations, and the X-ray tube voltage of the X-ray tube 3 is set to be the high X-ray tube voltage $E_H$ for one rotation in the first half, and the X-ray tube voltage of the X-ray tube 3 is set to be the low X-ray tube voltage $E_L$ for one rotation in the second half. Therefore, the X-ray controller 126 switches the X-ray tube voltage of the X-ray tube 3 from the high X-ray tube voltage $E_H$ to the low X-ray tube voltage $E_L$, simultaneously with the completion of the one rotation in the first half. The X-ray tube voltage may be set to be 140 kV (high X-ray tube voltage $E_H$) and 80 kV (low X-ray tube voltage $E_L$), which are representative X-ray tube voltage values.

An output signal from the X-ray detector 4 is converted into a digital signal by the DAS 128 of the data acquisition unit 114, and the signal is subjected to an air calibration process which is publicly known. Information regarding the X-ray attenuation coefficient, being obtained, is stored in the memory 123. The central processing unit 122 executes a publicly known CT image reconstructing program, thereby implementing an operation of the reconstruction unit 115, and generates a CT image representing the X-ray attenuation coefficient of the object.

The central processing unit 122 executes a publicly known separation program, thereby operating as the material separation unit 116, and applies the map for separation obtained in the input mode to the CT image being generated. Then, a material being associated with the X-ray attenuation coefficient of each region of the image is separated, and a separation image is obtained. The central processing unit 122 displays the separation image being calculated on the monitor 129, and simultaneously performs a highlighting process such as coloring the material in the separation image, in response to a directive from the operator, and provides the operator with the information regarding the material. It is further possible to establish connection between an external terminal and the image generation means 103, via a network such as the local area network, telephone line, the Internet, by means of a network adapter, so as to send and receive the CT image and the separation image therebetween.

In the imaging method as described above, the X-ray tube voltage is switched at high speed for each rotation to acquire measured data of X-rays having two or more types of energy spectra. However, it is possible to conduct the DE method according to a device configuration and an imaging procedure, which are different from those described above. By way of example, various methods are applicable such as those described in the following; a method where two pairs of the X-ray tube 3 and the X-ray detector 4 are provided in the gantry 5, and X-ray tube voltages different from each other are set on the respective X-line tubes 3, a method where a filter is provided in front of the X-line tube 3 or the X-line detector 4, and energy spectrum is changed according to whether or not the filter exists, a method where X-ray detector 4 having at least two layers are configured in such a manner as superimposed on the detection plane of the X-ray detector 4 in approximately vertical direction, thereby obtaining measured data according to the energy spectra being different on the respective layers of the X-ray detector 4, and a method where the tube voltage is switched at high speed every time when the rotating plate 6 is rotated at a predetermined rotation angle.

In the CT system according to the present embodiment, the map formation unit for separation 111 forms an optimum map for separation in response to the imaging condition inputted in the input unit of imaging condition 110 by the operator. Therefore, the material separation unit 116 is able to perform separation by using the optimum map for separation. Consequently, it is possible to enhance the separation accuracy, and processing for automatically separating the material may reduce the load on a radiologist.

It is to be noted that in the description above, there has been explained a method where in order to form the map for separation from the distribution of X-ray attenuation coefficient $\mu_k(x, y)$ of N materials, a material having the largest value of the distribution of X-ray attenuation coefficient $\mu(x, y)$ is selected for each pixel in the map for separation in step 204 of FIG. 4. However, the present invention is not limited to the method as described above. This will be explained in the following.

By way of example, when the map for separation is obtained as to each of the three materials 61, 62, and 63, the distribution of X-ray attenuation coefficient $\mu_1(x, y)$, $\mu_2(x, y)$, and $\mu_3(x, y)$ are obtained with respect to each of the materials, and if they are placed on the x-y plane, the arrangement is shown as FIG. 7(*a*). The distribution of X-ray attenuation coefficient $\mu_1(x, y)$, $\mu_2(x, y)$, and $\mu_3(x, y)$ are functions indicating the variation of the existing probability. Therefore, for example, the frequency of the X-ray attenuation coefficient of the materials 61 and 62 on the line 64 within the x-y plane is represented by the graph shown in FIG. 7(*b*) where the distribution of X-ray attenuation coefficients $\mu_1(x, y)$ and $\mu_2(x, y)$ overlap partially one another. Accordingly, depending on where the boundary 65 is placed between the area 51 associated with the material 61 and the area 52 associated with the material 62, it is possible to obtain the probability of erroneous separation between the material 61 and the material 62 (error rate). Therefore, it is possible to form an optimum map for separation by defining the boundary 65 on the place where the error rate becomes the lowest as to all the materials.

A principle will be explained to perform arithmetic processing to obtain the error rate from the distribution of X-ray attenuation coefficient. FIG. 8(*a*) shows the distribution of X-ray attenuation coefficient $\mu_k(x, y)$ 220 of the material k, and FIG. 8(*b*) shows the frequency of the $\mu_k(x, y)$ on the line 71 which is shown in FIG. 8(*a*). When the boundary 221 is set as shown in FIG. 8(*a*) and FIG. 8(*b*), a correct rate of the material k is represented by summation of the distribution of X-ray attenuation coefficient $\mu_k(X, y)$ contained in the area $S_k$ 72 including the average of attenuation coefficient ($\mu_{kaveL}$, $\mu_{kaveH}$) 222, i.e., the volume 223 within the area 72 of $\mu_k(x, y)$. On the other hand, the error rate of the material k is represented by the summation of the distribution of X-ray attenuation coefficient $\mu_k(x, y)$ contained in the area 73 other than the area $S_k$, i.e., the volume 224 within the area 73 of $\mu_k(x, y)$. Therefore, the error rate is expressed by the following formula 2.

$$1 - \int\int_{S_k} \mu_k ds \qquad \text{[Formula 2]}$$

A total error rate I for evaluating the separation accuracy for all the materials included in the map for separation can be defined by the following formula 3, in which the sum of squares of the error rate in each of the materials is standardized by the number of materials.

$$I = \sqrt{\frac{\sum_k \left(1 - \int\int_{S_k} \mu_k ds\right)^2}{\text{Number of Materials}}} \qquad \text{[Formula 3]}$$

Defining the boundary of each material to obtain the areas is performed so that the total error rate I represented by the above formula 3 is minimized, allowing an optimum map for separation to be calculated.

It is possible to employ various methods, as a means for defining the boundary to minimize the total error rate I. By way of example, as explained in the aforementioned step 204 (FIG. 4), there is a first method to be employed as the following; i.e., the method divides the x-y plane of the map for separation into minute areas (for example, pixels), and compares the frequencies of the distribution of X-ray attenuation coefficient $\mu_1(x, y)$, $\mu_2(x, y)$, $\mu_3(x, y)$, and so on, of the respective materials on the coordinates (x, y) of the minute areas (pixels). This method further selects the distribution of X-ray attenuation coefficient having the largest frequency, and decides the material (composition) of the distribution of X-ray attenuation coefficient being selected as the material (composition) of the minute area (pixel). Materials are determined, respectively associated with all the minute areas (pixels), and accordingly the map for separation can be generated. This method determines the related material for each minute area, and therefore it defines the boundary eventually without the need for conducting a calculation for deciding a position of the boundary. Therefore, even though the boundary position is not defined to calculate the total error rate I according to the position, it is possible to determine the map for separation which minimizes the total error rate I, and accordingly, there is an advantage that a volume of calculation can be reduced.

There is another method as the following as a second method; i.e., the method combines two distributions out of the distributions of X-ray attenuation coefficients $\mu_1(x, y)$, $\mu_2(x, y)$, $\mu_3(x, y)$, and so on, and depicts a boundary at a position where the two are crossing each other, i.e., where one frequency becomes equal to the other, thereby forming the map for separation. Also in the method, even though the total error rate I is not calculated, it is possible to determine the map for separation which minimizes the total error rate I. This method is applied in the second embodiment described in the following when the map for separation is determined.

It is further possible to employ another method as a third method, which defines a boundary at an arbitrary position, and calculates the total error rate I every time when the boundary is defined. This method, accordingly, defines the boundary position which minimizes the total error rate I by trial and error.

Next, an imaging experiment was conducted by using a phantom having the structure as shown in FIG. 9, in order to verify that the map for separation formed in step 201 to step 204 shown in FIG. 4 was optimized according to the present embodiment. Assuming a human body abdomen, the phantom had an oval-shaped cross section and it was made of urethane 151 having the attenuation coefficient being close to a clinical material. At the center and in the upper portion of the phantom, there were arranged cylindrical bodies respectively simulating the bone 152 and vessel filled contrast medium 150. The vessel filled contrast medium was filled with a material obtained by mixing a contrast medium into water. In here, there were prepared ten types of materials having different density.

In the imaging experiment, the map for separation was formed according to the imaging condition being configured in the input mode. Next, in the real imaging mode, X-rays having two types of energy were irradiated to perform imaging for obtaining an image of the X-ray attenuation coefficient, and by using the map for separation formed in the input mode, separation of a material was performed. The X-ray tube voltages $E_L$ and $E_H$ of the imaging condition were set to be 80 kV and 140 kV, respectively.

FIG. 10 shows the map for separation 156 calculated based on the imaging condition in the input mode according to the imaging experiment. It is found from the map for separation 156 in FIG. 10 that the x-axis represents an attenuation coefficient of lower X-ray energy, and the y-axis represents an attenuation coefficient of higher X-ray energy, and there are areas being divided by the boundary 221, into the urethane 154, the bone 155, and the vessel filled contrast medium 153. By applying the map for separation 156, in the actual measured data imaged in the real imaging mode, the urethane 151, the bone 152, and the vessel filled contrast medium 150 were separated, and by using the following formula 4, the total error rate $I_{res}$ was evaluated, regarding the three materials of the urethane 151, the bone 152, and the vessel filled contrast medium 150. The result of the evaluation is shown in FIG. 11.

$$I_{res} = \sqrt{\frac{\sum_k \left(1 - \frac{c_k}{p_k}\right)^2}{\text{Number of Materials}}} \quad \text{[Formula 4]}$$

$$1 - \frac{c_k}{p_k} \quad \text{[Formula 5]}$$

The total error rate $I_{res}$ for evaluation as expressed by the formula 4 described above is obtained by standardizing the sum of squares of the above formula 5 being the error rate for evaluation, by the number of materials, and the smaller $I_{res}$ value indicates the higher degree of separation accuracy. In the formula 4 and formula 5, "$p_k$" and "$c_k$" express respectively the total number of pixels in the material k in the separation image, and the number of pixels correctly separated.

As shown in FIG. 11, when the optimum map for separation 156 was applied according to the present embodiment, it is found that the total error rate for evaluation $I_{res}$ became lower and the separation accuracy was enhanced more, compared to the case where the map for separation of a conventional method was applied. It is to be noted that the imaging experiment can be conducted using an image generated by simulation, in addition to the method where an image is obtained by an actual imaging.

In the first embodiment as described above, the map for separation is formed every time when the operator performs an input operation. However, it is further possible to configure such that the map for separation is formed for each combination of the imaging condition being prepared in advance, and the map for separation being formed is stored in the storage unit of material parameters 112. With this configuration, there is an advantage that the map formation unit for separation 111 is able to acquire the map for separation just by referring to the storage unit of material parameters 112, thereby speeding up the arithmetic operation.

In the first embodiment, a clinical-use X-ray CT system is shown as a configuration example of the X-ray CT system. However, it is a matter of course that the present invention is applicable to an X-ray CT system which is used for a bomb test, a product nondestructive test, or the like. In the present embodiment, there is shown a configuration of a publicly known third-generation multi-slice X-ray CT system as one example. However, the present invention can be applied to a publicly known first, second, and fourth-generation X-ray CT system, and it is further applicable to a publicly known single-slice X-ray CT system and an electron beam CT.

Second Embodiment

A dual energy X-ray CT system according to a second embodiment will be explained. The configuration of the X-ray CT system according to the present embodiment is the same as the X-ray CT system of the first embodiment, but an operation for forming the map for separation by the map formation unit for separation 111 is different from that of the first embodiment.

The first embodiment is directed to a configuration where the map formation unit for separation 111 forms a map for separation (e.g., FIG. 5) that is divided into N areas respectively corresponding to N materials, when the operator designates via the input unit of imaging condition 110, N materials as the areas to be separated. However, if there are materials having similar distribution of X-ray attenuation coefficient μ(x, y), or the like, there is a possibility that the accuracy for separating two materials is low even though the formed map for separation is used. In such a case above, it is not possible to enhance the separation accuracy even though the map for separation being formed is employed.

In the present embodiment, if the separation accuracy between two materials is lower than a predetermined threshold, the two materials are assumed as the same material, and the areas on the map for separation respectively corresponding to the two materials are linked for clustering. Accordingly, the separation accuracy is enhanced.

By way of example, as shown in FIG. 12, on the map for separation which configures the area 160 associated with the material A, the area 161 associated with the material B, and the area 162 associated with the material C, if the separation accuracy between the material A and the material B is lower than the predetermined threshold, information 164 is generated for clustering both, and the material A 160 and the material B 161 are clustered as a material AB 163, thereby forming the map for separation 231.

Hereinafter, an explanation will be made with reference to steps 240 to 244 of the flowchart shown in FIG. 13, as to a procedure for forming the map by the map formation unit for separation 111. Firstly, the processing from steps 201 to 203 as shown in FIG. 4 according to the first embodiment is performed, and an X-ray attenuation coefficient μ(x, y) for each of N materials is obtained.

Next, a boundary of each material on the map for separation is decided. In here, there is employed a method in which pairs of two distributions are made, out of the distributions of X-ray attenuation coefficients of respective materials, $\mu_1(x, y)$, $\mu_2(x, y)$, and $\mu_3(x, y)$, and so on, and a boundary is depicted at a position where those two are crossing, i.e., where one frequency becomes equal to the other. Specifically, a material k of the separated target region is selected, and pairs are created using the material k and each of materials i which is not k (i=1, 2 ..., N; k≠i). Then, a boundary is depicted on the map for separation at a position where the distribution of X-ray attenuation coefficient of one of each pair becomes equal to that of the other (step 240). By way of example, as shown in FIG. 14(*a*), the material k 260 and the material A 261 are grouped into a pair, and a position of a valley is found out, where the distributions of X-ray attenuation coefficients $\mu(x, y)$ of the two materials are crossing, as shown in FIG. 14(*d*), and the boundary 263 is depicted on this position. On this occasion, the distributions of X-ray attenuation coefficients of the materials other than the pair are not taken into account.

Next, according to the aforementioned formula 3, the total error rate I is calculated as to the two materials k and A being in a pair (step 241), and the rate is compared with a predetermined threshold (step 242). If the calculated total error rate I is larger than the threshold, it indicates that the separation accuracy between the materials k and A is low. Therefore, it is decided that clustering is necessary at a subsequent time, and information of the material pair is stored in the memory 123 or the like, as clustering pair information 164 (step 245).

Similarly, as shown in FIG. 14(*b*), the boundary 263 is determined between a pair of the material k 260 and another material B 262 (step 240). The total error rate I is calculated as to the pair of the material k 260 and the material B 262, and it is determined whether or not the clustering is necessary. If it is necessary, the information is stored in the memory 123 or the like, as the clustering pair information 164 (steps 241, 242, and 245). These processing is performed as to the pairs, each of which is made up of the material k and each of all the other materials.

Next, as shown in FIG. 14(*c*), a product set (AND) of the boundary 263 between the material k 260 and one of the other materials (the material A 261 and the material B 262) is taken, and this product set is determined as an optimum boundary 264 of the material k 260 (step 243). In FIG. 14(*c*), the boundary determined by the AND processing is indicated by the solid line 264, and the boundary being rejected is indicated by the broken line 265. Accordingly, the boundary 264 surrounding the material k 260 can be determined. As thus described with the method for deciding the boundary 264 as to each material, it is possible to calculate the boundary at a high speed for any combination of clinical materials, even though the number of the materials is increased.

The processes from step 240 to step 245 are sequentially performed for the overall materials, thereby deciding the boundary surrounding each of the materials, and the map for separation (before clustering) as shown FIG. 12 is formed.

Next, in the step 245 mentioned above, the clustering pair information 164 is read out, which is stored in the memory 123 or the like. The boundary between the materials of the readout clustering pair is eliminated from the boundary of each of the pairs of the map for separation (before clustering), and the pair of materials is rendered to be one material (step 244). Accordingly, it is possible to cluster the materials having low separation accuracy, thereby allowing the map for separation (after clustering) to be formed, which is enhanced in the separation accuracy.

In the second embodiment, the map for separation is formed, in which two materials having low separation accuracy are clustered as one material. Therefore, the separation in the real imaging mode by using this map for separation may lower the total error rate I and enhance the separation accuracy.

A configuration has been explained, which determines in step 244 whether or not the clustering is necessary by using a threshold. However, if an operator desires the clustering between optional materials, it is possible to accept such information in step 201 and store the information as a cluster pair in step 245, so as to cluster the pair.

Third Embodiment

The dual energy X-ray CT system according to a third embodiment enables an imaging under an optimum X-ray condition. In the CT system according to the third embodiment, it is not necessary for an operator to input all of the imaging condition such as the separated target region, material, and dose, and only a partial condition is inputted. As for the part of the imaging condition that is not designated by the operator, the X-ray CT system generates multiple candidate values different in conditions variously in types, and forms a map for separation for each candidate value to obtain separation accuracy. Accordingly, while satisfying the imaging condition desired by the operator, it is possible to calculate an optimum X-ray condition having the highest degree of separation accuracy. In the real imaging mode, imaging can be performed under the optimum X-ray condition being calculated.

A structure of the dual energy X-ray CT system according to the third embodiment is similar to the structure according to the first embodiment as shown in FIG. 1. However, as shown in FIG. 15, in the input means 101, a calculation unit of X-ray condition 170 and a display unit of X-ray condition 171 are provided, in order to calculate and display the optimum X-ray condition. Therefore, this point is different from the configuration as shown in FIG. 1. The calculation unit of X-ray condition 170 incorporates a parameter storage unit of X-ray tube current quantity 172. Since other elements are the same as those of FIG. 1, tedious explanations will not be made. As a hardware configuration to implement the configuration of FIG. 15, for example, the central processing unit 122 of FIG. 2 according to the first embodiment expands and starts a predetermined program for processing operation of X-ray condition calculation, which is stored in the memory 123 in advance, thereby implementing the calculation unit of X-ray condition 170. For example, the memory 123 may constitute the parameter storage unit of X-ray tube current quantity 172. The monitor 129 of the image generation means 103 may also serve as the display unit of X-ray condition 171.

Hereinafter, the operation of the dual energy X-ray CT system according to the third embodiment will be explained. In the X-ray CT system of the present embodiment, the input mode and the real imaging mode are prepared, as in the case of the first embodiment. Hereinafter, the input mode will be explained with reference to the flowchart as shown in FIG. 16.
(1) Set Imaging Condition The calculation unit of X-ray condition 170 displays on the monitor 129, a screen for inputting the imaging condition as shown in FIG. 17. This screen is to accept settings of the imaging condition as to the following three elements; the select list of separating region 130, the select list of separating material 131, and the select dose mode 180. The operator uses the mouse 121, the keyboard 120, and the like, to configure the settings of the imaging condition (step 270 in FIG. 16).

The present embodiment, in particular, enables setting of the X-ray condition by a dose, instead of the X-ray tube voltage and the quantity of X-ray tube current, and therefore, setting by the select dose mode 180 is available. Since the settings for the select list of separating region 130 and the select list of separating material 131 are the same as the first embodiment, tedious explanations will not be made. In the select dose mode 180, a selection is accepted from the operator, which selects one from two modes; a low exposure mode and a high quality image mode. The low exposure mode is to perform the DE method, at a dose equivalent to a normal imaging using X-rays including one type of energy spectrum, which is not the DE method. On the other hand, the high quality image mode is to acquire a high SN image by performing the DE method using more dose than the normal imaging. Predetermined doses $R_{total}$ are allocated to the low exposure mode and the high quality image mode, respectively. Therefore, the operator is allowed to select the dose, without inputting any numerical values as the dose.

It is to be noted that a method for setting the select dose mode 180 is not limited to the aforementioned setting manner. It is further possible to configure such that a numerical value entry field is displayed on the screen for allowing the operator to input the dose as a numerical value. The dose indicated here is assumed as including an irradiated dose, an exposed dose, and the like. A configuration allowing as least a setting of three elements; the separated target region, the material, and the dose, is sufficient as the screen shown in FIG. 17. However, other configuration may be applicable. In addition, if the imaging condition is stored in advance, it is not necessary for the operator to input the condition each time.

(2) Calculate Optimum X-Ray Condition

Next, on the basis of the imaging condition including the separated target region, the material, and the select dose mode 180, which is inputted in step 270, the calculation unit of X-ray condition 170 obtains multiple combinations (candidate values) of the X-ray condition (i.e., a dose ratio between higher X-ray energy and lower X-ray energy, the X-ray tube voltage and the quantity of X-ray tube current for this occasion) satisfying this imaging condition (step 271 to step 273 in FIG. 16).

Firstly, the dose is fractionated, and multiple dose candidate values are obtained (step 271). Specifically, it is obtained according to the following procedure. Doses $R_{total}$ being predetermined numerical values, are respectively associated in advance with the low exposure mode and the high quality mode, any selected by accepting the input from the operator via the input unit of imaging condition 110. Since the dose $R_{total}$ corresponds to a sum of the lower energy X-lay and the higher X-ray energy, the calculation unit of X-ray condition 170 fractionates the dose $R_{total}$ of the selected mode into the X-ray doses $R_L$ and $R_H$, respectively associated with the lower X-ray energy and the higher X-ray energy. As a way of fractionation, it is possible to employ a method the dose $R_{total}$ is multiplied by one of predefined fractionating ratios being various in types.

Next, multiple candidate values are set for the X-ray tube voltages $E_L$ and $E_H$, respectively for the time of lower X-ray energy irradiation and higher X-ray energy irradiation (step 272). By way of example, there is a method to set the X-ray tube voltages $E_L$ and $E_H$ by increasing from a predetermined lowest voltage, by the amount being predefined, and there is also another method to set the X-ray tube voltage $E_L$ and $E_H$ by sequentially selecting an X-ray tube voltage from a predefined multiple types of X-ray tube voltages. It is further possible to configure such that the operator inputs multiple types of combination of the X-ray tube voltages $E_L$ and $E_H$, via the input unit of imaging condition 110.

Next step configures a setting of multiple candidate values as the quantity of X-ray tube current $I_L$ and $I_H$ (step 273). The parameter storage unit of X-ray tube current quantity 172 within the calculation unit of X-ray condition 170 stores in the form of table, the quantities of X-ray tube current respectively associated with combinations of the dose and the X-ray tube voltage, being obtained in advance. The calculation unit of X-ray condition 170 accesses the parameter storage unit of X-ray tube current quantity 172, and reads out the quantities of X-ray tube current $I_L$ and $I_H$, respectively associated with the combinations ($E_L$, $R_L$) and ($E_H$, $R_H$) including the multiple types of candidate values of the X-ray tube voltages $E_L$ and $E_H$ being set or inputted in step 272, and the multiple types of candidate values of the dose $R_L$ and $R_H$ being set in step 271. Accordingly, the setting is made as to the multiple candidate values of the quantity of X-ray tube current.

The map formation unit for separation 111 calculates the map for separation for each of the multiple combinations of candidates (step 274). The process for calculating the map for separation is the same as the steps 201 to 204 of the first embodiment as shown in FIG. 4. The total error rate I for map formation is calculated for each of the map for separations being formed, by using the formula 3 shown in the first embodiment (step 275). A map for separation is selected, whose value I being obtained is the minimum among the calculated total error rates I, and the combination of the candidate values ($E_L$, $R_L$, $I_L$), ($E_H$, $R_H$, $I_H$) used for calculating the map for separation is determined as the optimum X-ray condition (step 276). Accordingly, in response to the optional setting configured by the operator, it is possible to calculate the optimum map for separation and the optimum X-ray condition constantly.

The calculation unit of X-ray condition 170 displays on the display unit of X-ray condition 171, the optimum X-ray condition ($E_L$, $R_L$, $I_L$), ($E_H$, $R_H$, $I_H$) and the total error rate I, decided in the aforementioned step 276. When the operator gives a directive to perform imaging under this X-ray condition, the imaging under this optimum X-ray condition is performed in the real imaging mode. It is further possible to configure such that if the total error rate I under the optimum X-ray condition which is determined in step 276 is equal to or less than a threshold predefined by the operator, the real imaging mode is started automatically without waiting for a directive from the operator, to perform imaging. If the total error rate I is over the aforementioned threshold, it is possible to display on the display unit of X-ray condition 171, "X-ray irradiation is disapproved".

With the configuration above, in the real imaging mode, imaging is performed under the optimum X-ray condition, and it is possible to generate a material separation image by using the map for separation with the minimum total error rate I.

As thus described, it is not necessary for the CT system according to the third embodiment to enter parameters of all the X-ray condition. As for the dose ratio between the higher X-ray energy and the lower X-ray energy, and the X-ray tube voltage and the quantity of X-ray tube current for each of the X-rays, optimum values may be obtained by calculation to minimize the total error rate I of the map for separation, from the candidate values satisfying the imaging condition inputted by the operator, and the optimum values may be presented to the operator. Therefore, it is possible to perform imaging under the X-ray condition which minimizes the total error rate I, and the separation of a material can be executed using the map for separation with the minimum total error rate I. Accordingly, a high degree of separation accuracy and reduction of dose can be achieved.

In the present embodiment, an imaging experiment was conducted in order to verify whether or not the optimum X-ray condition was determined. In the imaging experiment, a phantom similar to that of FIG. 9 according to the first embodiment was employed. As a method for setting the candidate values of the X-ray tube voltages $E_L$ and $E_H$ in step 272, two types of X-ray tube voltage were selected as $E_L$ and $E_H$, out of predetermined three types of X-ray tube voltages (80 kV, 120 kV, and 140 kV). It is to be noted that such candidate values of the X-ray tube voltage as described above are not limited to those values.

As the select dose mode 180 set in step 207, the low exposure mode was selected. Accordingly, the total dose $R_{total}$ was set to be equivalent to the dose of a normal imaging (imaging with the X-ray having one-type energy spectrum), which is not the DE method. As for the dose ratio between the lower X-ray energy and the higher X-ray energy, set in step 271, the dose ratio of the low X-ray tube voltage of the total dose $R_{total}$ was made to vary from 0 to 1, as indicated by the horizontal axis of FIG. 18. With the configuration above, multiple maps for separation were calculated, and the total error rate for evaluation $I_{res}$ was calculated according to the formula 4 as described above, for each map for separation being calculated.

FIG. 18 shows a graph indicating the variation of the total error rate $I_{res}$, when the dose ratio (dose of the low X-ray tube voltage in the total dose) was changed. As shown in FIG. 18, the graph indicating the variation of the total error rate I showed the minimum value when the dose ratio was changed, in any of the combinations of the X-ray tube voltages. In the example shown in FIG. 18, the total error rate for evaluation $I_{res}$ became the minimum when the X-ray tube voltage $E_L$ was 80 kV and $E_H$ was 140 kV, and the dose ratio (dose of the low X-ray tube voltage of the total dose) was 0.45 (plot 280). Accordingly, it was confirmed that the dose ratio and the X-ray tube voltage at the plot 280 were selected as the optimum X-ray condition.

It is to be noted that upon plotting a graph in FIG. 18, the total error rate for evaluation $I_{res}$ may be obtained and plotted for each of the dose ratios at any sampling intervals, and by interpolating between the plots using an approximation curve, the minimum value of the $I_{res}$ may be calculated at high speed.

As thus described, the dual energy X-ray CT system of the third embodiment is able to calculate an X-ray condition which minimizes the total error rate, in response to the dose designated by the operator, and perform the real imaging under the condition. Therefore, it is possible to acquire a highly accurate separation image by the DE method, under the X-ray condition where the dose is reduced. Furthermore, the optimum X-ray condition is displayed for the operator, allowing the operator to perform imaging under a desired condition.

Here, an explanation has been made regarding a configuration to set the irradiated dose by the operator, but another configuration is applicable where not only the irradiated dose, but also a total exposure to an object is available for setting.

In the third embodiment, the separated target region and the total dose are inputted to calculate the optimum X-ray condition (the X-ray tube voltage and the quantity of X-ray tube current), but it is a matter of course that calculating only the optimum quantity of X-ray tube current is possible by accepting an entry of the X-ray tube voltage from the operator.

It is further possible to employ Monte Carlo simulation or database of energy spectrum, to calculate an energy spectrum and total photon count from the optimum X-ray tube voltage and quantity of X-ray tube current. Therefore, instead of calculating the optimum X-ray tube voltage and the quantity of X-ray tube current, it is also possible to calculate the energy spectrum and the total photon count.

In the third embodiment, every time when the operator makes entries, candidate values of the X-ray condition are obtained and calculation of the map for separation is conducted. However, it is further possible to form a map for separations for a combination of the imaging conditions prepared in advance and store the map in the storage unit of material parameters 112. Accordingly, the map for separation can be acquired just by referring to the storage unit of material parameters 112 in the map formation unit for separation 111, and therefore there is an advantage that the arithmetic processing can be performed at a higher speed.

In the third embodiment, the clinical X-ray CT system is taken as an example, but it is a matter of course that the present invention is applicable to an X-ray CT system which is used for a bomb test, a nondestructive test, or the like. In the present embodiment, there is shown a configuration of a publicly known third-generation multi-slice X-ray CT system as one example. However, the present invention can be applied to a publicly known first, second, and fourth-generation X-ray CT system, and it is further applicable to a publicly known single-slice X-ray CT system and an electron beam CT.

In the present invention, as in the first embodiment and the second embodiment, it is possible to form an optimum map for separation based on the imaging condition such as a separated target region and X-ray tube voltage. Therefore, a high degree of separation accuracy can be achieved by applying the optimum map for separation. Further, as in the third embodiment, it is also possible to calculate an optimum X-ray condition, and therefore reduction of dose can also be achieved.

DENOTATION OF REFERENCE NUMERALS

Figure 1:
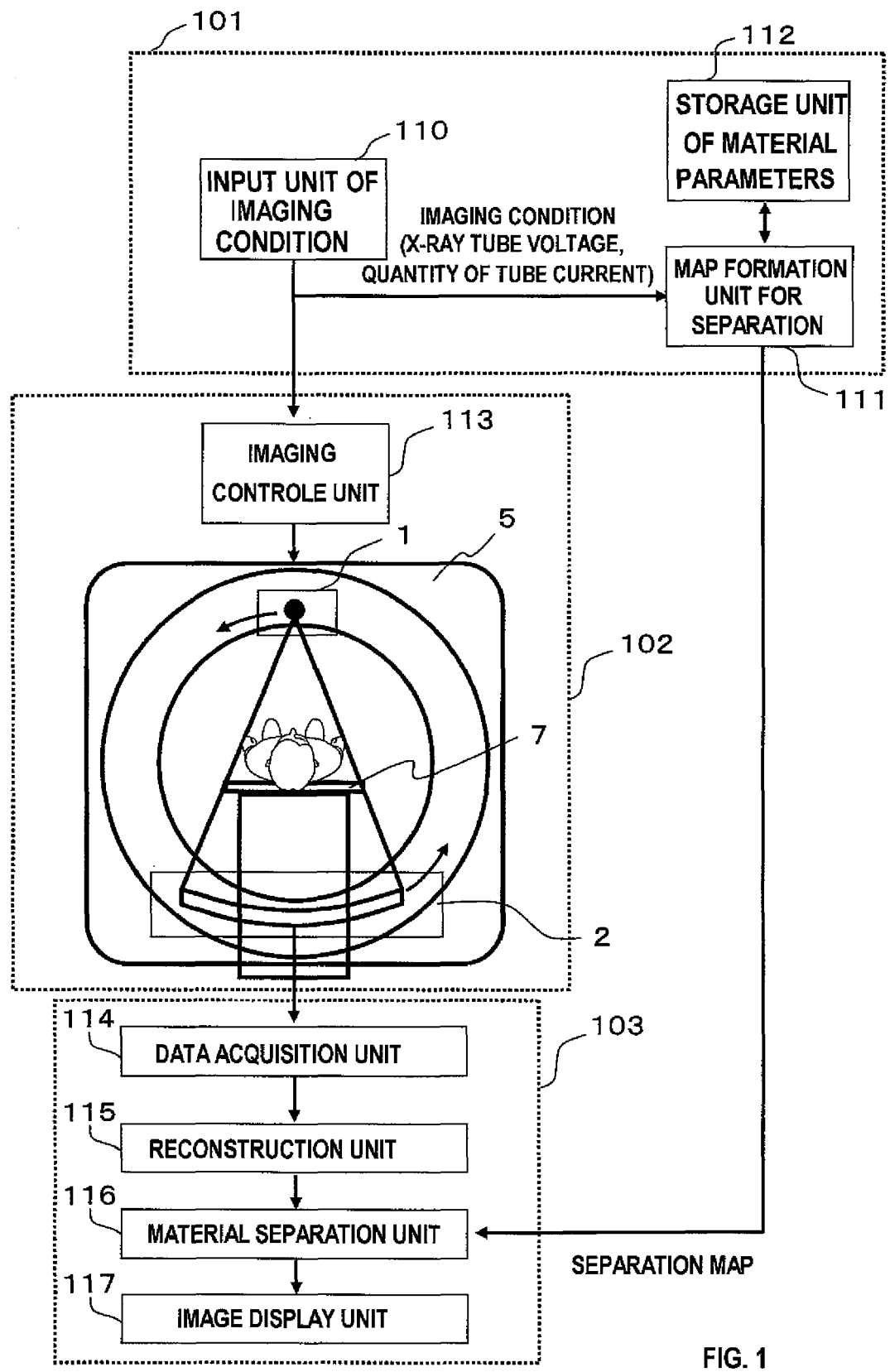
FIG. 1 is a block diagram for explaining an overview of the X-ray CT system according to the first embodiment.
Figure 2:
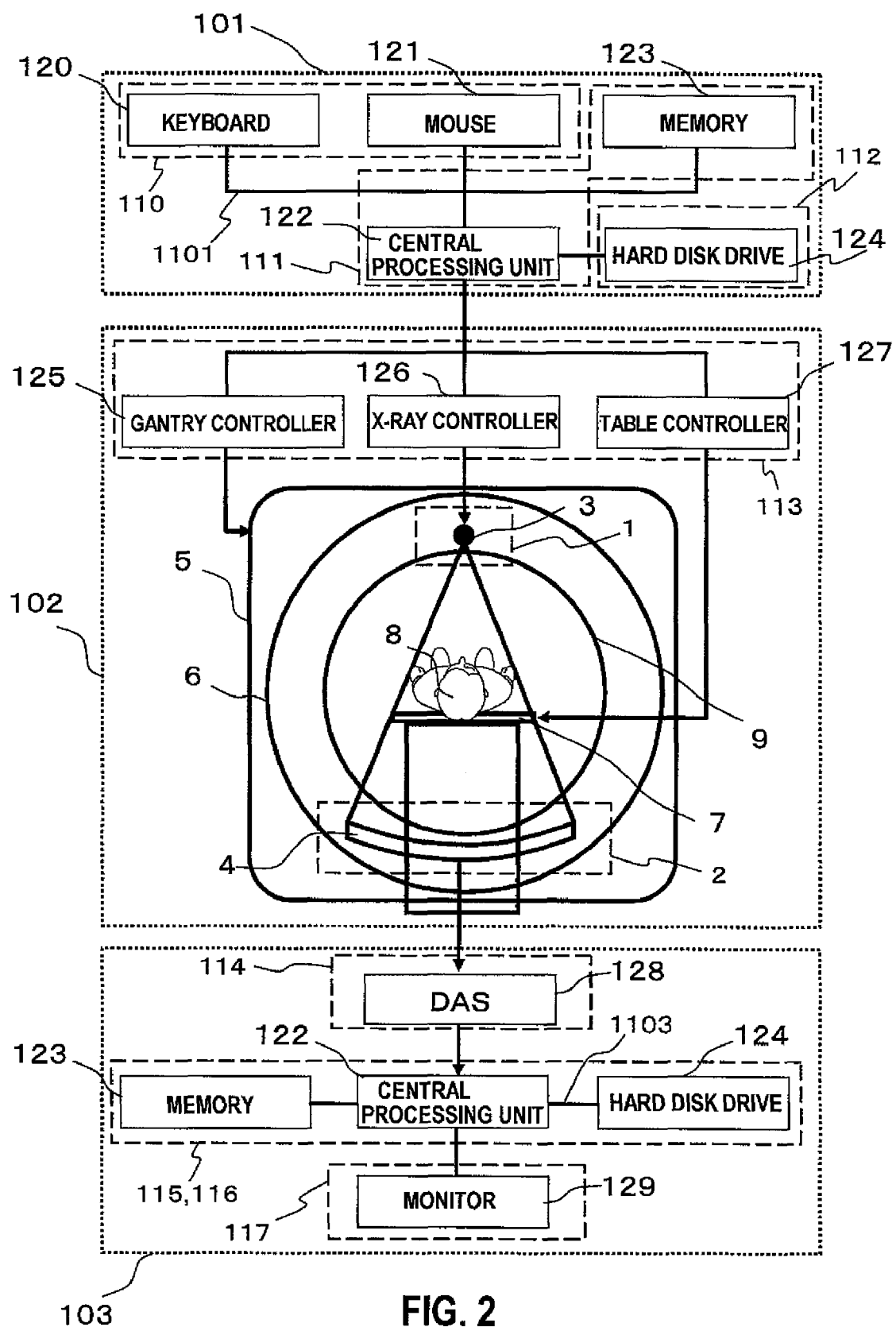
FIG. 2 is a block diagram showing a hardware configuration which implements the X-ray CT system according to the first embodiment.
Figure 3:
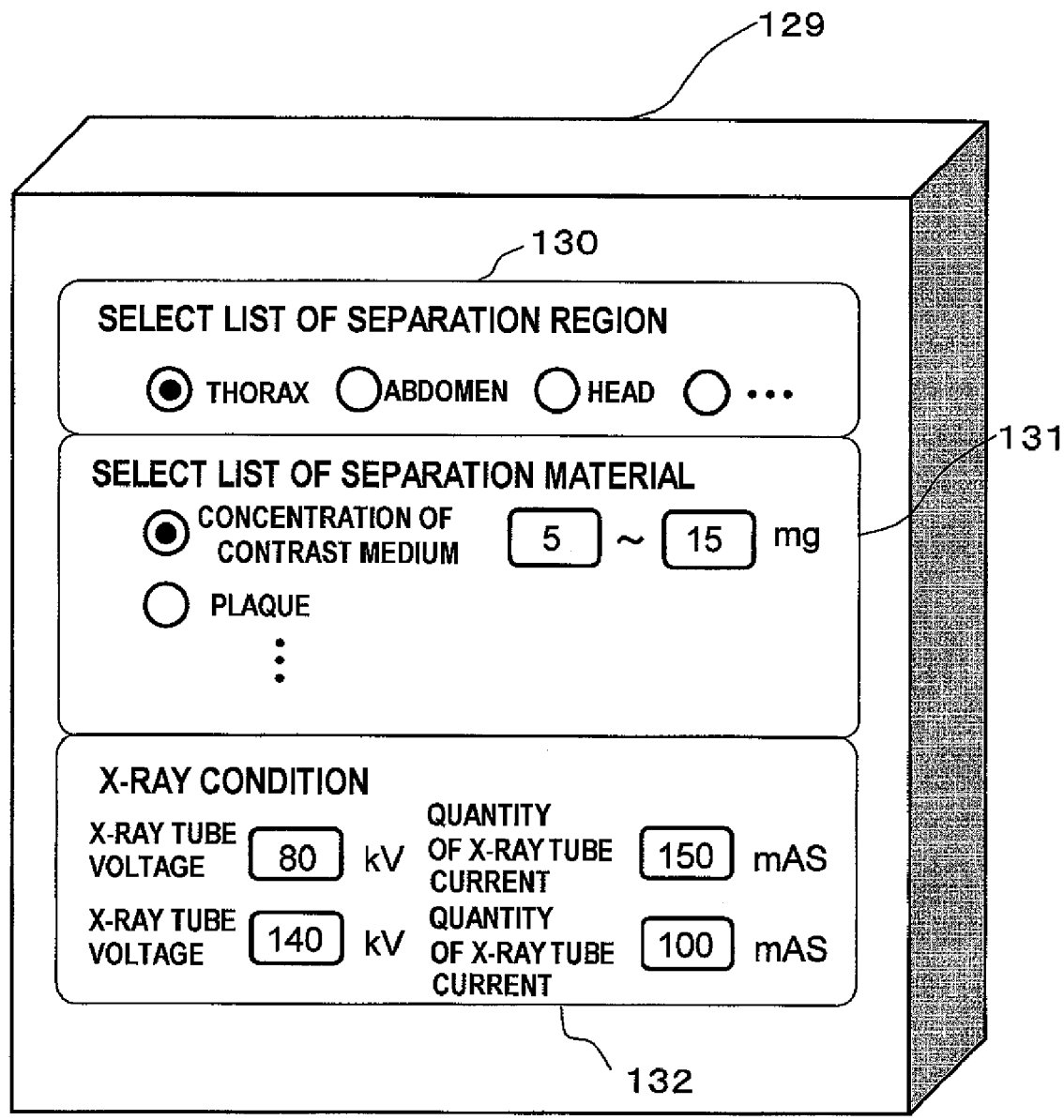
FIG. 3 illustrates a screen example which is displayed by the input unit of imaging condition 110 of the X-ray CT system according to the first embodiment.
Figure 4:
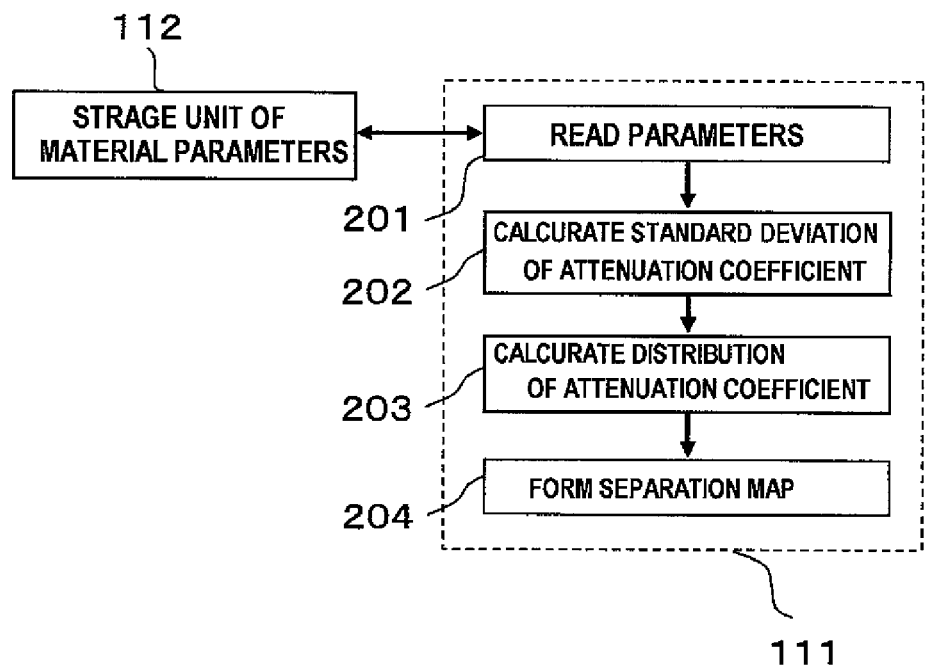
FIG. 4 is a flowchart which shows an operation of the map formation unit for separation in the X-ray CT system according to the first embodiment.
Figure 5:
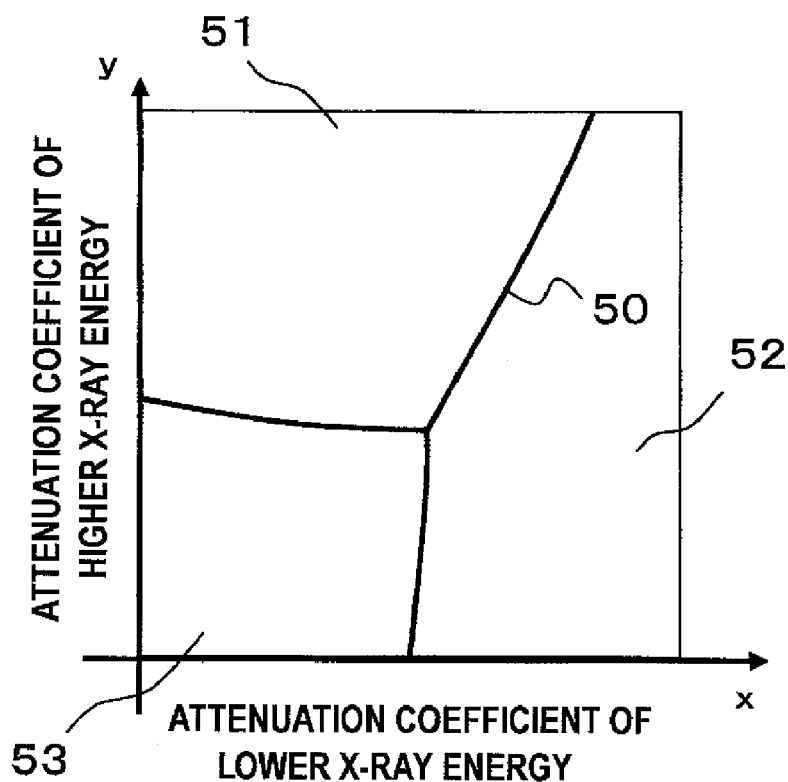
FIG. 5 illustrates one example of the map for separation which is formed by the X-ray CT system according to the first embodiment.
Figure 6:
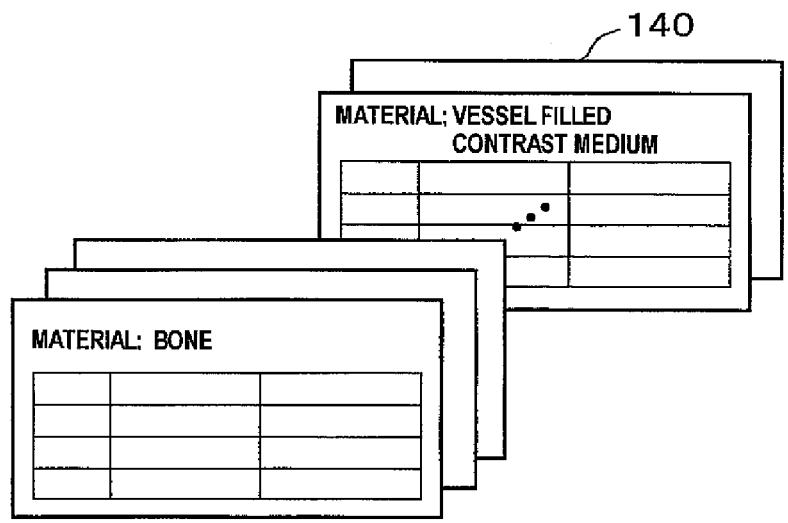
FIG. 6 illustrates information within the tables stored in the storage unit of material parameters 112 in the X-ray CT system according to the first embodiment.
Figure 7:
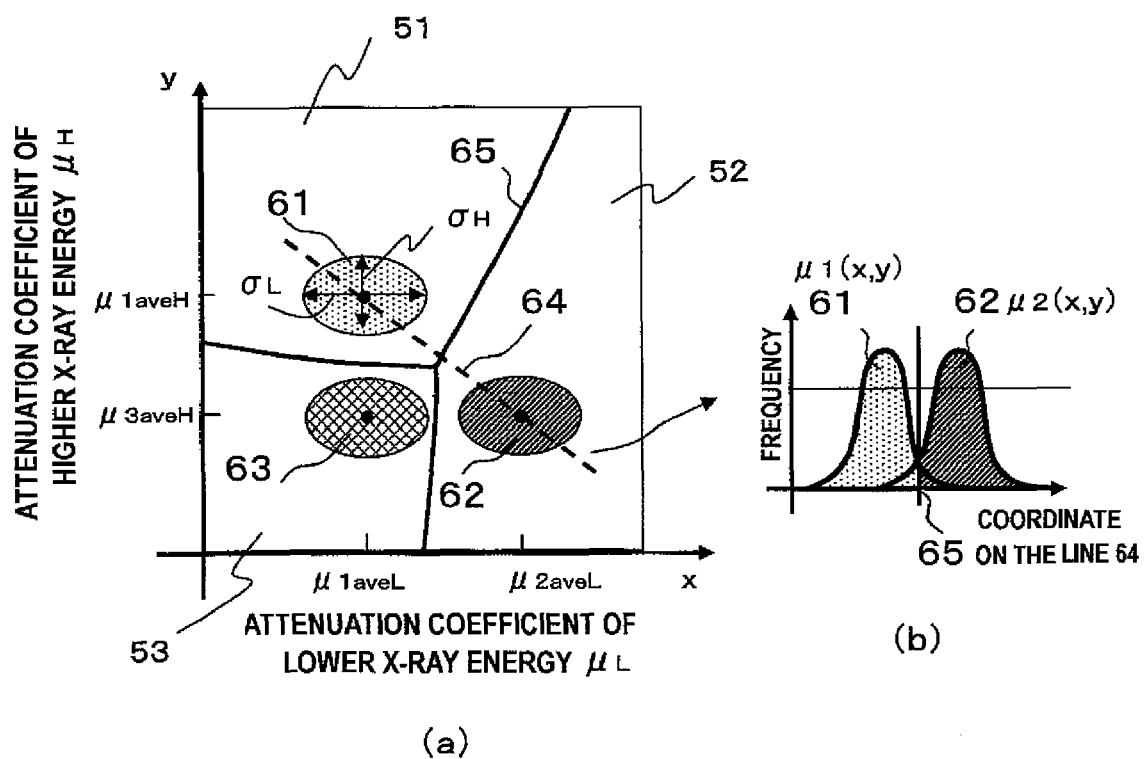
FIG. 7(a) and FIG. 7(b) illustrate that the boundary of the map for separation shown in FIG. 5 is decided based on the existing probability (a distribution of X-ray attenuation coefficient)
Figure 8:
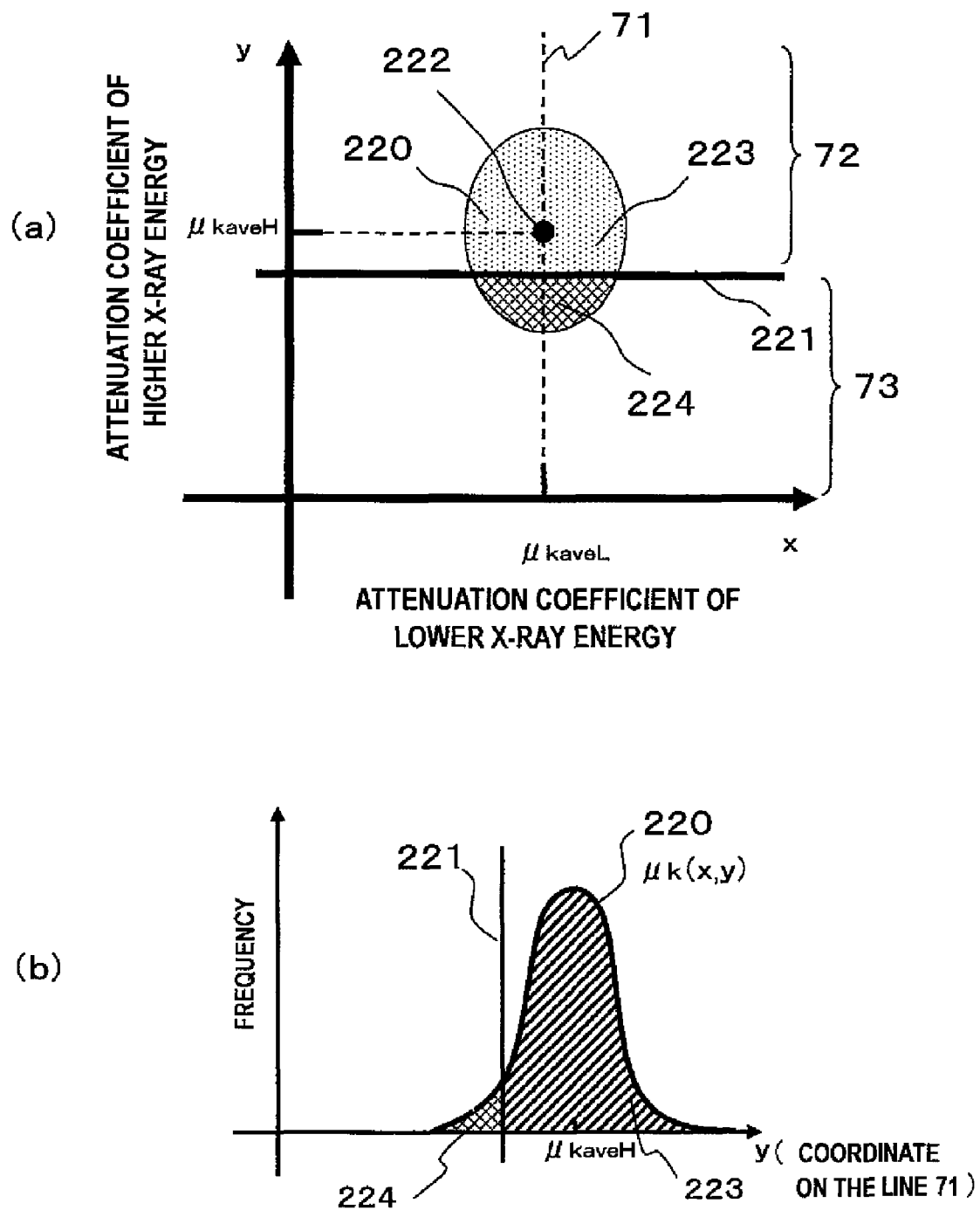
FIG. 8(a) and FIG. 8(b) illustrate the relationship between the distribution of X-ray attenuation coefficient and the boundary 221 being set, on the map for separation as shown in FIG. 5.
Figure 9:
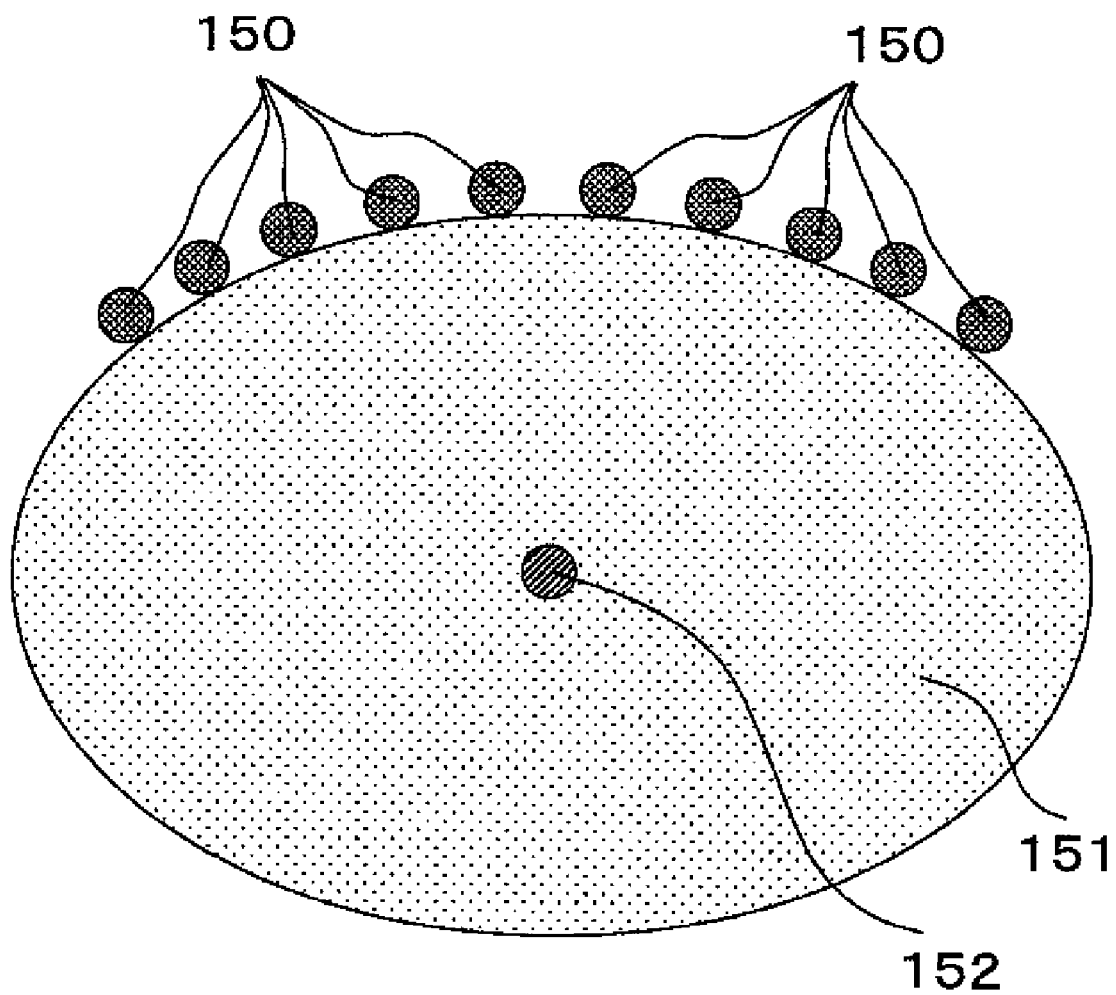
FIG. 9 is a sectional view of the phantom used in the confirmation experiment according to the first embodiment.
Figure 10:
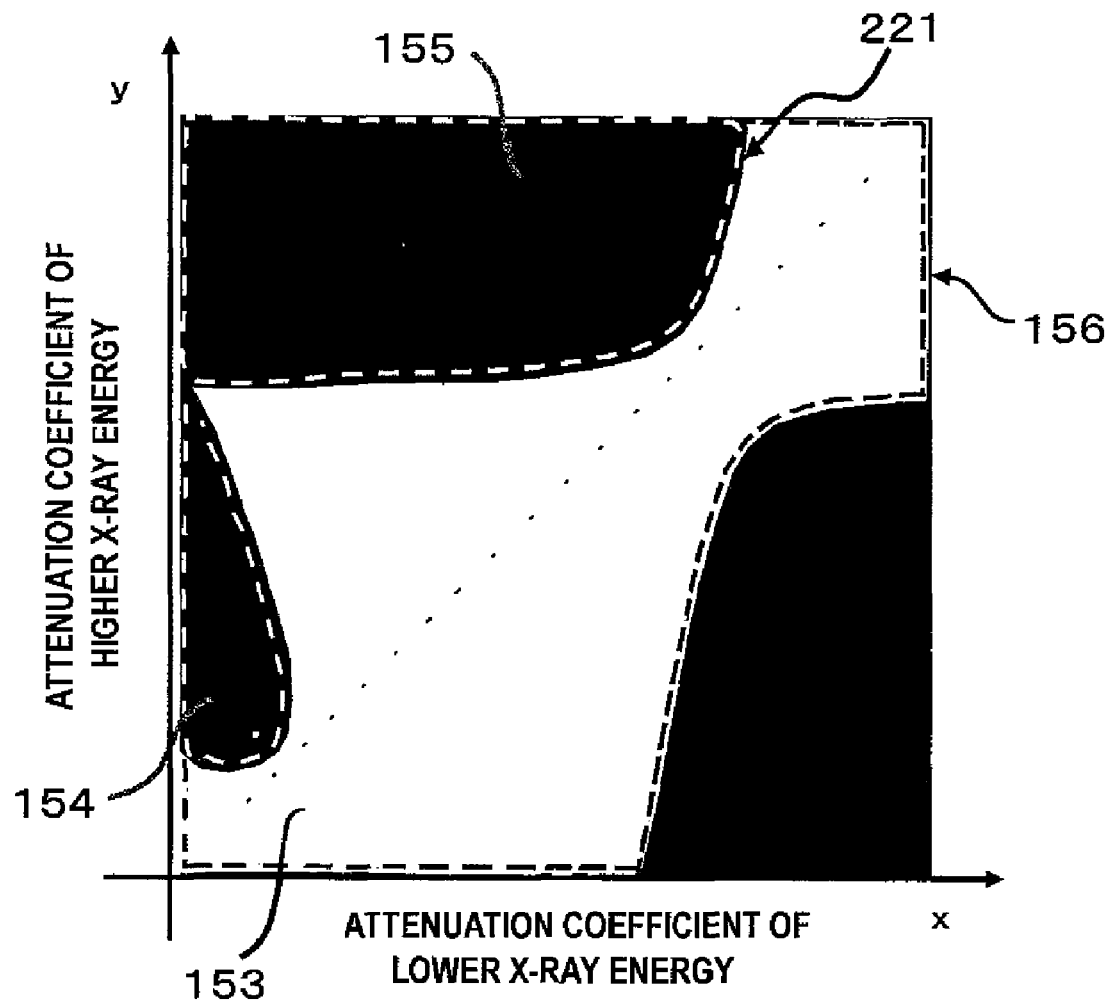
FIG. 10 illustrates the map for separation formed in the confirmation experiment according to the first embodiment.
Figure 11:
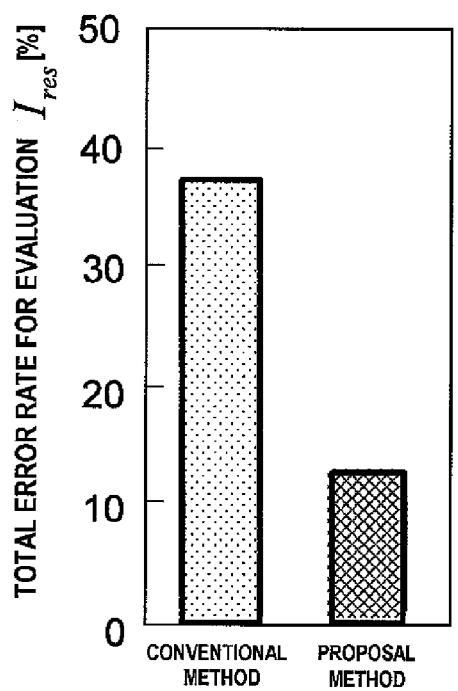
FIG. 11 is a graph indicating the total error rate for evaluation $I_{res}$ of the map for separation formed in the confirmation experiment according to the first embodiment.
Figure 12:
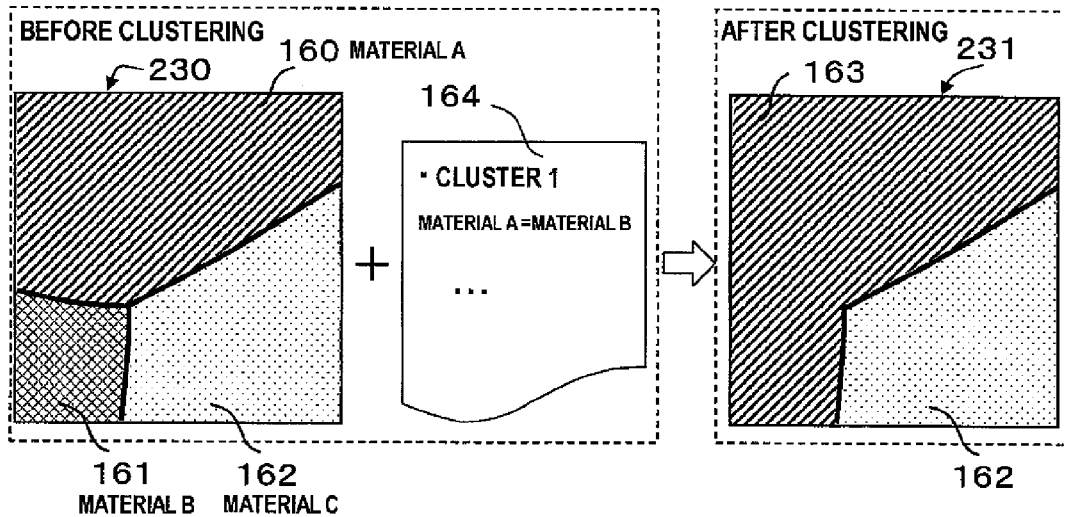
FIG. 12 illustrates the clustering of areas in the map for separation in the X-ray CT system according to the second embodiment.
Figure 13:
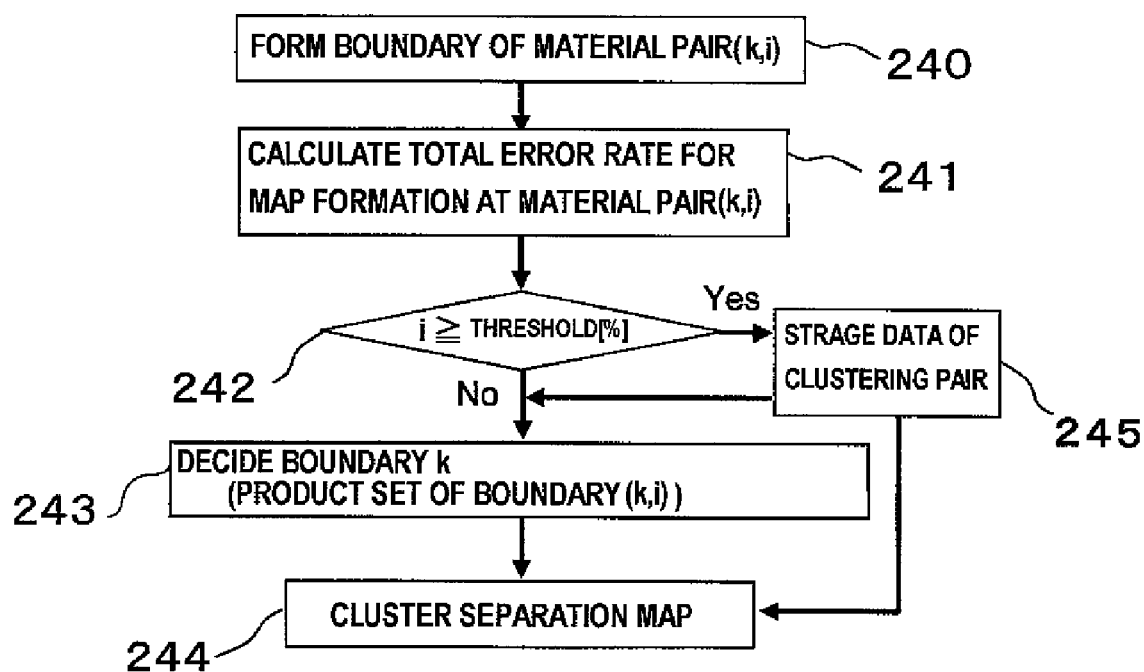
FIG. 13 is a flowchart showing the operation of the X-ray CT system according to the second embodiment.
Figure 14:
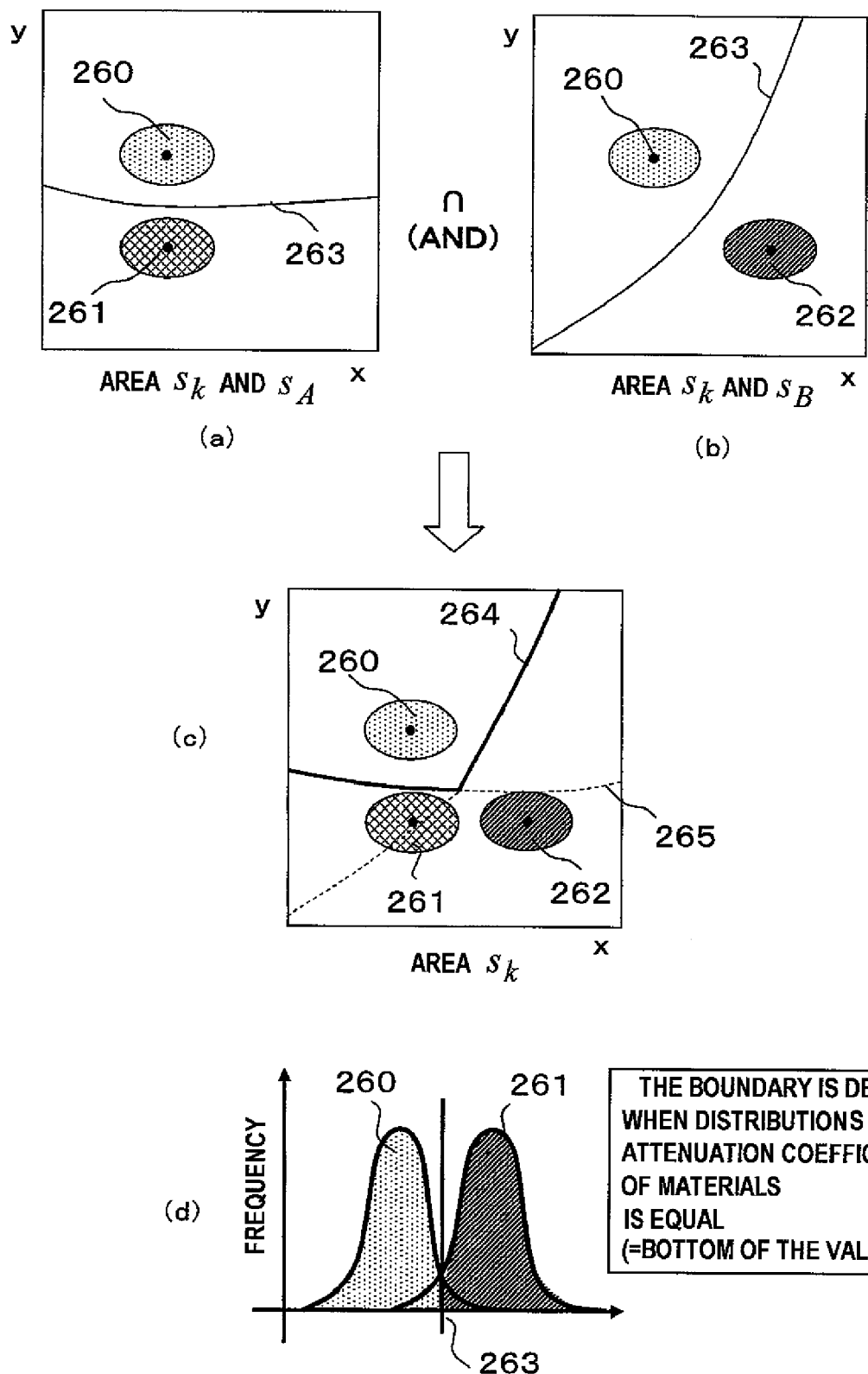
FIG. 14(a) and FIG. 14(b) illustrates the material pair and a boundary therebetween on the map for separation.
FIG. 14(c) illustrates that the boundary of the material 260 is determined based on a product set (AND) of the boundary of the material pair.
FIG. 14(d) illustrates that the boundary line is decided when the distribution of attenuation coefficient is at the bottom of the valley.
Figure 15:
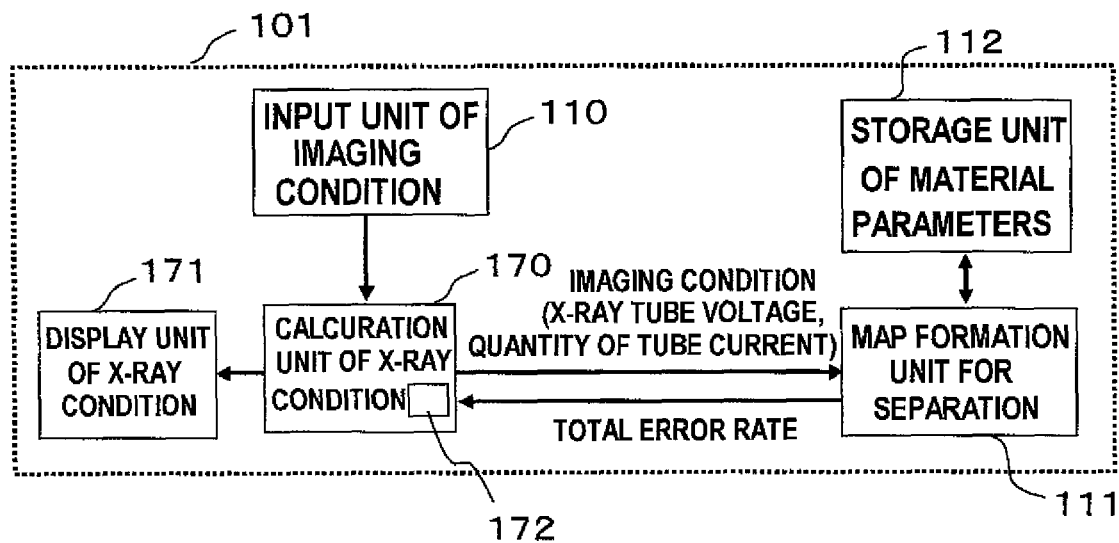
FIG. 15 is a block diagram showing the configuration of the input means 101 of the X-ray CT system according to the third embodiment.
Figure 16:
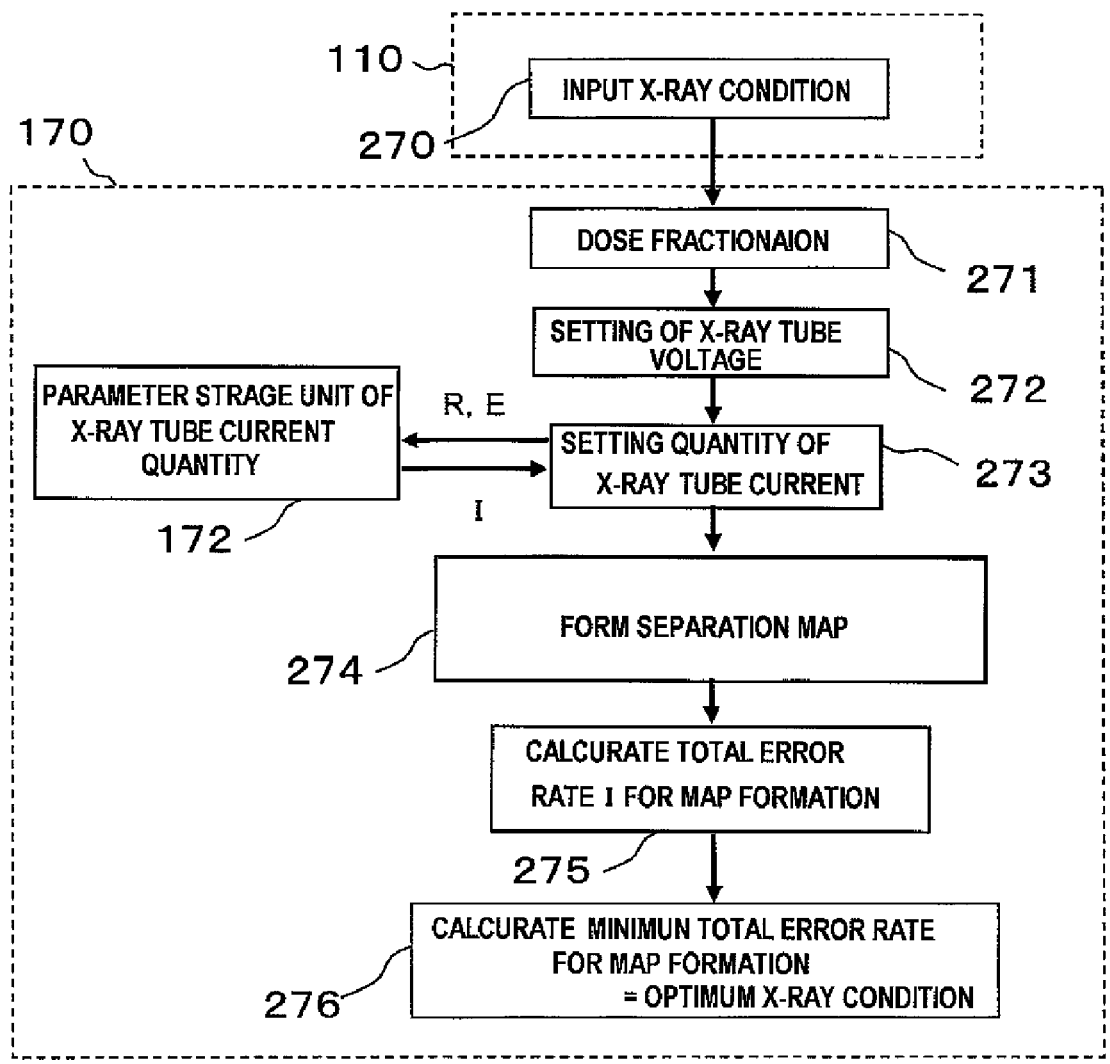
FIG. 16 is a flowchart showing the operation of the calculation unit of X-ray condition 170 of the X-ray CT system according to the third embodiment.
Figure 17:
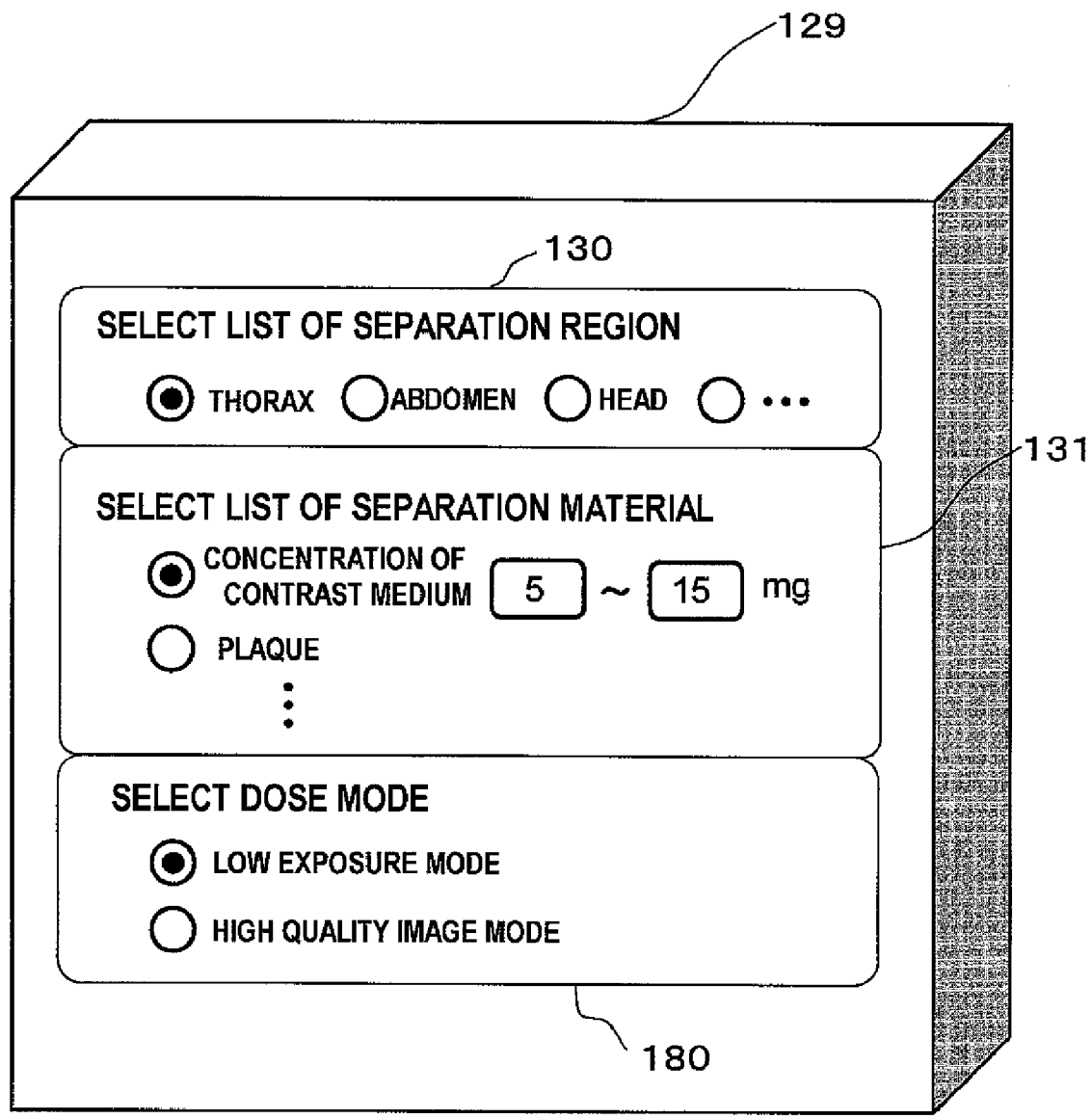
FIG. 17 illustrates a screen example which is displayed by the input unit of imaging condition 110 of the X-ray CT system according to the third embodiment.
Figure 18:
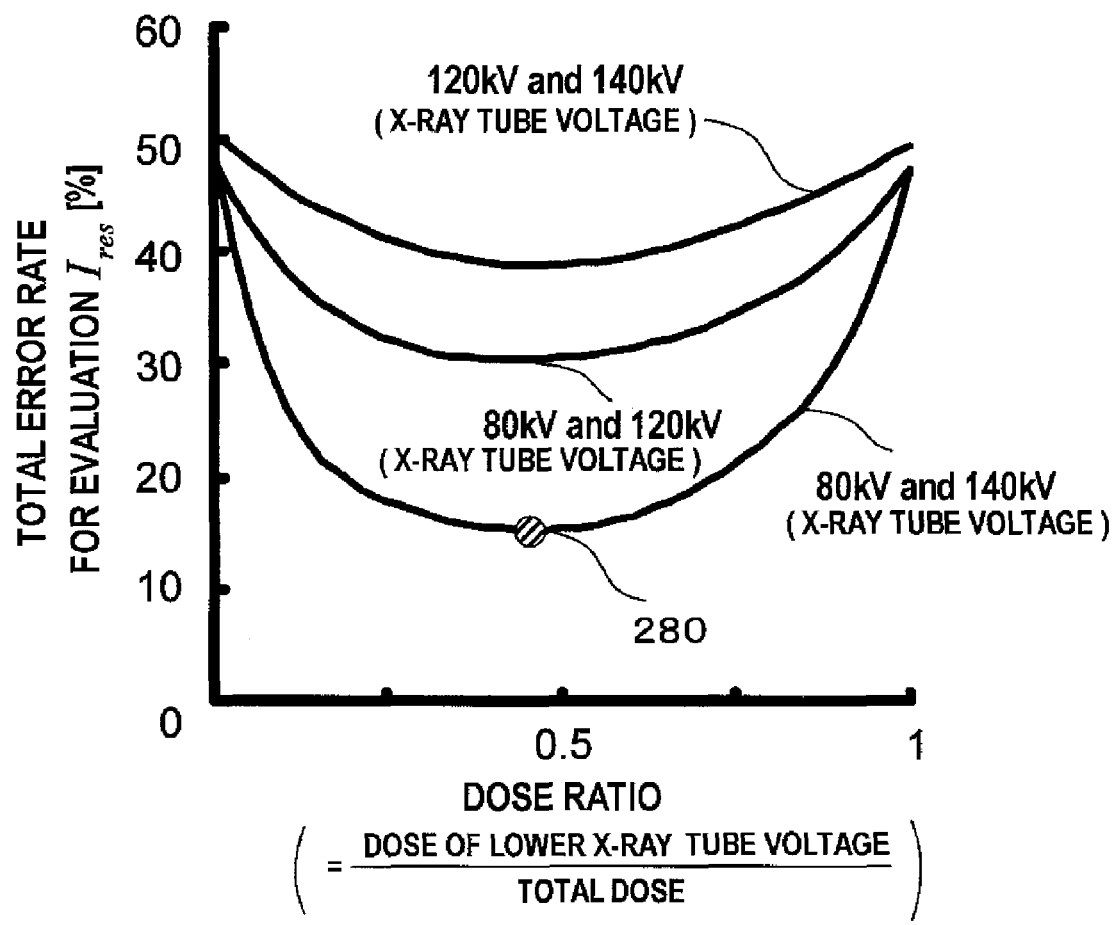
FIG. 18 is a graph showing the relationship between the dose ratio and the total error rate for evaluation $I_{res}$, obtained by the confirmation experiment according to the third embodiment, as to each combination of the X-ray tube voltages.

1 ... X-RAY IRRADIATION UNIT
2 ... X-RAY DETECTION UNIT
3 ... X-RAY TUBE
4 ... X-RAY DETECTOR
5 ... GANTRY
6 ... ROTATING PLATE
7 ... TABLE
8 ... OBJECT
9 ... CIRCULAR APERTURE
10 ... INPUT MEANS
102 ... IMAGING MEANS
103 ... IMAGE GENERATION MEANS
110 ... INPUT UNIT OF IMAGING CONDITION
111 ... MAP FORMATION UNIT FOR SEPARATION
112 ... STORAGE UNIT OF MATERIAL PARAMETERS
113 ... IMAGING CONTROL UNIT
114 ... DATA ACQUISITION UNIT
115 ... RECONSTRUCTION UNIT
116 ... MATERIAL SEPARATION UNIT
117 ... IMAGE DISPLAY UNIT
120 ... KEYBOARD
121 ... MOUSE
122 ... CENTRAL PROCESSING UNIT
123 ... MEMORY
124 ... HDD
125 ... GANTRY CONTROLLER
126 ... X-RAY CONTROLLER
127 ... TABLE CONTROLLER
128 ... DAS
129 ... MONITOR
130 ... SELECTION LIST OF SEPARATING REGION
131 ... SELECTION LIST OF SEPARATING MATERIAL
132 ... X-RAY CONDITION INPUT AREA
140 ... TABLE OF MATERIAL
141 ... TABLE OF MATERIAL (MATERIAL OF BONE)
142 ... TABLE OF MATERIAL (MATERIAL OF VESSEL FILLED CONTRAST MEDIUM)
150 ... VESSEL FILLED CONTRAST MEDIUM
151 ... URETHANE
152 ... BONE
153 ... AREA OF VESSEL FILLED CONTRAST MEDIUM
154 ... AREA OF URETHANE
155 ... AREA OF BONE
156 ... MAP FOR SEPARATION
160 ... AREA OF MATERIAL A
161 ... ARE OF MATERIAL B
162 ... AREA OF MATERIAL C
163 ... MATERIAL AB
164 ... CLUSTERING PAIR
170 ... CALCULATION UNIT OF X-RAY CONDITION
171 ... DISPLAY UNIT OF X-RAY CONDITION
172 ... PARAMETER STORAGE UNIT OF X-RAY TUBE CURRENT QUANTITY
180 ... SELECT DOSE MODE

What is claimed is:

1. An X-ray CT system comprising,
an X-ray irradiation unit for irradiating X-rays having multiple types of different energy spectra,
an X-ray detection unit for detecting the X-rays after passing through an object,
an image calculation unit for calculating an image of X-ray attenuation coefficients respectively for the multiple types of X-rays based on each detection signal from the X-ray detection unit,
a separation calculator for applying to a map for separation which indicates a relationship between multiple types of X-ray attenuation coefficients and a composition of the object, values of the X-ray attenuation coefficients in association with a corresponding area in the image of multiple types of X-ray attenuation coefficients, so that the composition of the area is separated,
a map formation unit for separation for forming the map for separation, and
an input unit for accepting from an operator, an input regarding an X-ray irradiation condition of the X-ray irradiation unit and multiple compositions to be separated, wherein,
the map formation unit for separation performs arithmetic processing to obtain existing probabilities of the multiple compositions under the X-ray irradiation condition being inputted in the input unit, and forms the map for separation based on the existing probabilities.

2. The X-ray CT system according to claim 1, wherein,
the map formation unit for separation has a configuration to calculate the existing probabilities of multiple compositions with respect to each combination of the multiple types of X-ray attenuation coefficients, and determine a composition having the largest existing probability as a composition corresponding to the combination of the X-ray attenuation coefficients, thereby forming the map for separation.

3. The X-ray CT system according to claim 1, wherein,
the map formation unit for separation obtains functions, each indicating a variation of the existing probability of each of the compositions, under the X-ray irradiation condition being inputted in the input unit, assuming the multiple types of X-ray attenuation coefficients as variables, depicts as a boundary, a position where the functions each indicating the variation of the existing probability of each of the compositions are crossing, in the space of the map for separation with coordinate axes respectively of the multiple types of X-ray attenuation coefficients, and accordingly, forms the map for separation in which multiple areas separated by the boundary correspond to the multiple compositions, respectively.

4. The X-ray CT system according to claim 3, wherein, the map formation unit for separation obtains a ratio of erroneous determination occurrence as to the compositions respectively associated with two areas separated by the boundary, by calculation using the function indicating the variation of the existing probabilities of the two compositions, the position of the boundary, and a predetermined formula, and combines the areas associated with the two areas on the map for separation when the ratio of erroneous determination occurrence is larger than a predetermined threshold, so that these areas are separated as one composition.

5. The X-ray CT system according to claim 3, wherein, the input unit accepts settings as to only a part of the X-ray condition, which is necessary for forming the map for separation, the map formation unit for separation generates multiple candidate values as to the other part of the X-ray irradiation condition, then, the maps for separation are formed for the multiple candidate values respectively, and as to each of the multiple types of maps for separation being obtained, the ratio of erroneous determination occurrence is obtained as to the composition in all the maps for separation, by calculation using the function indicating the variation of the existing probability, the position of the boundary, and a predetermined formula, thereby allowing the map for separation having the minimum ratio of erroneous determination occurrence to be selected, and further allowing the candidate value for the selected map for separation to be selected as an optimum value of the X-ray irradiation condition.

6. The X-ray CT system according to claim 5, wherein, the optimum value of the X-ray irradiation condition being selected is displayed, indicating that this value is the optimum X-ray irradiation condition.

7. The X-ray CT system according to claim 5, wherein, the X-ray irradiation unit performs irradiation of X-rays using the optimum value of the X-ray condition, so as to acquire the image of X-ray attenuation coefficient.

8. The X-ray CT system according to claim 5, wherein, the map formation unit for separation generates a candidate value for each of the multiple types of X-rays, at least as to the quantity of X-ray tube current of the X-ray irradiation unit.

9. The X-ray CT system according to claim 5, wherein, the input unit accepts a setting of total irradiated dose of multiple types of X-rays, as the X-ray irradiation condition, and the map formation unit for separation generates candidate values of irradiated dose respectively for the multiple types of X-rays, so that the total amount of the irradiated dose of the multiple types of X-rays satisfies the total irradiated dose being set.

10. The X-ray CT system according to claim 5, wherein, the input unit accepts a setting of exposed dose according to multiple types of X-rays, and the map formation unit for separation generates candidate values of irradiated dose respectively for the multiple types of X-rays, so that the total exposure on the object who is subjected to the irradiation of the multiple types of X-rays corresponds to the exposed dose.

11. The X-ray CT system according to claim 1, wherein, the map formation unit for separation obtains functions, each indicating a variation of the existing probability of each of the compositions, under the X-ray irradiation condition being inputted in the input unit, assuming the multiple types of X-ray attenuation coefficients as variables, depicts a boundary at a predetermined position based on the functions each indicating the variation of the existing probability, in the space of the map for separation with coordinate axes respectively of the multiple types of X-ray attenuation coefficients, and accordingly, forms the map for separation in which multiple areas separated by the boundary correspond to the multiple compositions, respectively.

12. The X-ray CT system according to claim 11, wherein, the map formation unit for separation has a configuration to obtain error rates as to all the compositions according to a predetermined formula, by using the function indicating the variation of the existing probability and the position of the boundary, and determines the position where the error rate is minimized as the position of the boundary.

13. The X-ray CT system according to claim 1, wherein, the map formation unit for separation comprises a data storage unit which stores in advance, an average of X-ray attenuation coefficient and a standard deviation of the X-ray attenuation coefficient, with respect to each X-ray irradiation condition, as to the multiple compositions acceptable by the input unit, reads out from the data storage unit, the average of X-ray attenuation coefficient and the standard deviation of the X-ray attenuation coefficient associated with the X-ray irradiation condition accepted from an operator by the input unit, and substitutes the read information into a predetermined formula, thereby obtaining the existing probability by calculation.

14. The X-ray CT system according to claim 13, wherein, the input unit accepts a setting of an X-ray tube voltage and a quantity of X-ray tube current with respect to each of the multiple types of X-rays as the X-ray irradiation condition,
the data storage unit stores the average of X-ray attenuation coefficient for each X-ray tube voltage acceptable by the input unit and the standard deviation of the X-ray attenuation coefficient per quantity of X-ray tube current,
the map formation unit for separation uses the standard deviation of the X-ray attenuation coefficient per quantity of X-ray tube current, the quantity of X-ray tube current set in the input unit, and a predetermined formula, thereby obtaining the standard deviation of the X-ray attenuation coefficient by calculation.

* * * * *